US005728807A

United States Patent [19]
Shiloh et al.

[11] Patent Number: 5,728,807
[45] Date of Patent: Mar. 17, 1998

[54] MUTATED PROTEINS ASSOCIATED WITH ATAXIA-TELANGIECTASIA

[75] Inventors: Yosef Shiloh, Tel Aviv, Israel; Danilo A. Tagle, Gaithersburg; Francis S. Collins, Rockville, both of Md.

[73] Assignee: Ramot-University Authority For Applied Research and Industrial Development, Ltd., Tel Aviv, Israel

[21] Appl. No.: 493,092

[22] Filed: Jun. 21, 1995

Related U.S. Application Data

[63] Continuation-in-part of Ser. No. 441,822, May 16, 1995.

[51] Int. Cl.$^6$ .......................... C07K 14/00; C07K 14/435
[52] U.S. Cl. .......................... 530/350; 530/324; 530/326; 536/23.1; 536/23.5; 536/23.2
[58] Field of Search .......................... 530/350, 324, 530/326; 536/23.1, 23.5

[56] References Cited

U.S. PATENT DOCUMENTS

| | | | |
|---|---|---|---|
| 3,791,932 | 2/1974 | Schuurs et al. | 195/103.5 R |
| 3,839,153 | 10/1974 | Schuurs et al. | 195/103.5 R |
| 3,850,578 | 11/1974 | McConnell | 23/230 B |
| 3,850,752 | 11/1974 | Schuurs et al. | 195/103.5 |
| 3,853,987 | 12/1974 | Dreyer | 424/1 |
| 3,867,517 | 2/1975 | Ling | 424/1 |
| 3,879,262 | 4/1975 | Schuurs et al. | 195/63 |
| 3,901,654 | 8/1975 | Gross | 23/230 B |
| 3,935,074 | 1/1976 | Rubenstein et al. | 195/103.5 R |
| 3,984,533 | 10/1976 | Uzgiris | 424/12 |
| 3,996,345 | 12/1976 | Ullman et al. | 424/12 |
| 4,034,074 | 7/1977 | Miles | 424/1 |
| 4,098,876 | 7/1978 | Piasio et al. | 424/1 |
| 4,736,866 | 4/1988 | Leder et al. | 800/1 |
| 4,879,219 | 11/1989 | Wands et al. | 435/7 |
| 5,011,771 | 4/1991 | Bellet et al. | 435/7.94 |
| 5,175,383 | 12/1992 | Leder et al. | 800/2 |
| 5,175,384 | 12/1992 | Krimpenfort et al. | 800/2 |
| 5,175,385 | 12/1992 | Wagner et al. | 800/2 |
| 5,221,778 | 6/1993 | Bryne et al. | 800/2 |
| 5,281,521 | 1/1994 | Trojanowski et al. | 435/7.5 |
| 5,288,846 | 2/1994 | Quertermous et al. | 435/172.3 |
| 5,298,422 | 3/1994 | Schwartz et al. | 435/320.1 |
| 5,347,075 | 9/1994 | Sorge | 800/2 |
| 5,360,735 | 11/1994 | Weinshank et al. | 435/240.2 |
| 5,387,742 | 2/1995 | Cordell | 800/2 |
| 5,395,767 | 3/1995 | Murnane et al. | 435/320.1 |

FOREIGN PATENT DOCUMENTS

| | | |
|---|---|---|
| WO9314200 | 7/1993 | WIPO. |
| WO9400572 | 1/1994 | WIPO. |
| WO9406908 | 3/1994 | WIPO. |
| WO9423049 | 10/1994 | WIPO. |
| WO9428123 | 12/1994 | WIPO. |
| WO9503431 | 2/1995 | WIPO. |

OTHER PUBLICATIONS

Aksentijevich et al., "Familial mediterranean fever in Moroccan Jews: demonstration of a founder effect by extended haplotype analysis" *Am. J. Hum. Genet.*, 53:644–651 (1993).

Ambrose et al., "A physical map across chromosome 11q22–q23 containing the major locus for ataxia telangiectasia" *Genomics*, 21:612–619 (1994).

Attree et al., "The Lowe's oculocherebronrenal syndrome gene encodes protein highly homologous to inositol polphosphate ..." *Nature*, 358:239–242 (1992).

Barker, "A more robust, rapid alkaline denaturation sequencing method" *BioTechniques*, vol. 14, No. 2, pp. 168–169 (1993).

Berger et al., "Isolation of a candidate gene for Norrie disease by positional cloning" *Nature Genet.*, 1:199–203, (1992).

Buckler et al., "Exon amplification: a strategy to isolate mammalian genes based on RNA splicing" *Proc. Natl. Acad. Sci. USA*, 88:4005–4009 (1991).

Burke and Olson, "Preparation of clone libraries in yeast artificial–chromosome vectors" in *Methods in Enzymology*, vol. 194, eds. Guthrie and Fink, Academic Press, Inc., Chap. 17, pp. 251–270 (1991).

Capecchi et al., "Altering the genome by homologous recombination" *Science*, 244:1288–1292 (1989).

Chakravari et al., "Nonuniform recombination within the human β-globin gene cluster" *Am. J. Hum. Genet.*, 36:1239–1258 (1984).

Chelly et al., "Isolation of a candidate gene for Menkes disease that encodes a potential heavy metal binding protein" *Nature Genet.*, 3:14–19 (1993).

Church et al., "Isolation of genes from complex sources of mammalian genomic DNA using exon amplification" *Nature Genet.*, 6:98–104 (1993).

Collins, "Positional cloning: let's not call it reverse anymore" *Nature Genet.*, 1:3–6 (1992).

Davies et al., "Targeted alterations in yeast artificial chromosomes for inter–species gene transfer" *Nucleic Acids Research*, vol. 20, No. 11, pp. 2693–2698 (1992).

Dickinson et al., "High frequency gene targeting using insertional vectors" *Human Molecular Genetics*, vol. 2, No. 8, pp. 1299–1302 (1993).

Duyk et al., "Exon trapping: a genetic screen to identify candidate transcribed sequences in cloned mammalian genomic DNA" *Proc. Natl. Acad. Sci. USA*, 87:8995–8999 (1990).

Foroud et al., "Localization of an ataxia–telangiectasia locus to a 3–cm interval on chromosome 11q23..." *Am. J. Hum. Genet.*, 49:1263–1279 (1991).

(List continued on next page.)

*Primary Examiner*—Stephen Walsh
*Assistant Examiner*—Eliane Lazar-Wesley
*Attorney, Agent, or Firm*—Kohn & Associates

[57] ABSTRACT

A purified and isolated gene, designated ATM, mutations of which cause ataxia-telangiectasia.

5 Claims, 1 Drawing Sheet

OTHER PUBLICATIONS

Frohman, "On beyond classic RACE (rapid amplification of cDNA ends)" *PCR Methods and Applications*, 4:S40–S58 (1994).

Frohman et al., "Rapid production of full–length cDNAs from rare transcripts: amplification using a single gene–specific..." *Proc. Natl. Acad. Sci. USA*, 85:8998–9002 (1988).

Gatti et al., "Genetic haplotyping of ataxia–telangiectasis families localizes the major gene to an 850 kb region..." *Int. J. Radiat. Biol.*, vol. 66, No. 6, S57–S62 (1994).

Gatti et al. "Localization of a taxia–telangiectasia gene to chromosome 11q22–23" *Nature*, 336:577–580 (1988).

Gilboa et al., "Transfer and expression of cloned genes using retroviral vectors" *BioTechniques* 4(6):504–512 (1986).

Hastbacka et al., "Linkage disequilibrium mapping in isolated founder populations: diastrophic dysplasia in Finland" *Nature Genet.*, 2:204–211 (1992).

Hogervorst et al., "Rapid detection of BRCA1 mutations by the protein truncation test" *Nature Genetics*, 10:208–212 (1995).

Huxley et al., "The human HPRT gene on a yeast artificial chromosome is functional when transferred to mouse cells..." *Genomics*, 9:742–750 (1991).

Jakobovits et al., "Germ–line transmission and expression of a human–derived yeast artificial chromosome" *Nature*, vol. 362, pp. 255–258 (1993).

James et al., "A radiation hybrid map of 506 STS markers spanning human chromosome 11" *Nature Genet.*, 8:70 (1994).

Kawasaki, ES. "Amplification of RNA". in PCR Protocols: A guide to methods and applications, Innis et al., editors. *Academic Press*, pp. 21–27 (1990).

Kerem et al., "Identification of the cystic fibrosis gene: genetic analysis" *Science*, 245:1073–1080 (1989).

Lamb et al., "Introduction and expression of the 400 kilobase precursor amyloid protein gene in transgenic mice" *Nature Genetics*, vol. 5, pp. 22–29 (1993).

Lange et al., "Localization of an ataxia–telangiectasia gene to a 500 kb interval on chromosome 11q23.1 by linkage analysis..." *Am. J. Hum. Genet.*, S7:112–119 (1995).

Lehesjoki et al., "Localization of the EPM1 gene for progressive myoclonus epilepsy on chromosome 21..." *Hum. Mol. Genet.*, 2:1229–1234 (1993).

Lichter et al., "High–resolution mapping of human chromosome 11 by in situ hybridization with cosmid clones" *Science*, 247:64–69 (1990).

Litt and Luty, "A hypervariable microsatellite revealed by in vitro amplification of a dinucleotide repeat within the cardiac muscle" *Am. J. Hum. Genet.*, 44:397–401, (1989).

Llerena et al., "Spontaneous and induced chromosome breakage in chorionic villus samples: a cytogenetic approach..." *J. Med. Genet.*, 26:174–178 (1989).

Lovett et al., "Direct selection: A method for the isolation of cDNAs encoded by large genomic regions" *Proc. Natl. Acad. Sci. USA*, 88, pp. 9628–9632 (1991).

McConville etal., "Genetic and physical mapping of the ataxia–telangiectasia locus on chromosome 11q22–q23" *Int. J. Radiat. Biol.*, vol. 66, No. 6, S45–S56 (1994).

McConville etal., "Paired STSs amplified from radiation hybrids, and from associated YACs, identify highly polymorphic loci..." *Hum. Mol. Genet.*, 2:969–974 (1993).

McConville et al., "Fine mapping of the chromosome 11q22–23 region using PFGE, linkage and haplotype analysis..." *Nucleic Acids Res.*, 18:4335–4343 (1990).

Miki et al., "A strong candidate for the breast and ovarian cancer susceptibility gene BRCA1" *Science*, 266:66–71 (1994).

Mitchison et al., "Fine genetic mapping of the batten disease locus (CLN3) by haplotype analysis..." *Genomics*, 16:455–460 (1993).

Morgan et al., "The selective isolation of novel cDNAs encoded by the regions surrounding the human interleukin 4 and 5 genes" *Nucleic Acids Res.*, 20:5173–5179 (1992).

Orita et al., "Detection of polymorphisms of human DNA by gel electrophoresis as single–strand conformation polymorphisms" *Proc. Natl. Acad. Sci. USA*, 86:2766–2770 (1989).

Oskato et al., "Ataxia–telangiectasia: allelic association with 11q22–23 markers in Moroccan–Jewish patients" *43rd Annual Meeting of the American Society of Human Genetics*, New Orleans, LA (1993).

Ozelius et al., "Strong alleleic association between the torsion dystonia gene (DYT1) and loci on chromosome..." *Am. J. Hum. Genet.*, 50:619–628 (1992).

Parimoo et al., "cDNA selection: efficient PCR approach for the selection of cDNAs encoded in large chromosomal DNA fragments" *Proc. Natl. Acad. Sci. USA*, 88:9623–9627 (1991).

Pease et al., "Light–generated oligonucleotide arrays for rapid DNA sequence analysis" *Proc. Natl. Acad. Sci. USA*, 91(11):5022–5026 (1994).

Rothstein, "Targeting, disruption, replacement, and allele rescue..." in *Methods in Enzymology*, Guthrie and Fink, editors, Academic Press, Inc., Chap. 19, pp. 291–301 (1991).

Rotman et al., "Three dinucleotide repeat polymorphisms at the ataxia–telangiectasia locus" *Human Molecular Genetics*, vol. 3, No. 11, pp. 2079 (1994b).

Rotman et al., "A YAC contig spanning the ataxia–telangiectasia locus (groups A and C) at 11q22–q23" *Genomics*, 24:234–242 (1994c).

Rotman et al., "Physical and genetic mapping at the ATA/ATC locus on chromosome 11q22–23" *Int. J. Radiat. Biol.*, vol. 66, No. 6, S63–S66 (1994d).

Savitsky et al., "A single ataxia–telangiectasia gene with a product similar to PI–3 kinase" *Science*, 268:1749–1753 (23 Jun. 1995).

Schedl et al., "A yeast artifical chromosome covering the tyrosinase gene confers copy number–dependent expression in transgenic mice" *Nature*, vol. 362, pp. 258–261 (1993).

Sirugo et al., "Friedreich ataxia in Louisiana acadians: demonstration of a founder effect by analysis of microsatellite..." *Am. J. Hum. Genet.*, 50:559–566 (1992).

Shiloh, "Ataxia–telangiectasia: closer to unraveling the mystery" *European Journal of Human Genetics*, (1995).

Shiloh et al., "Genetic, physical and functional analysis of the ataxia–telangiectasia locus..." *Am. J. Hum. Genet.*, 55 (suppl.), A49 (1994).

Strauss et al., "Germ line transmission of a yeast artificial chromosome spanning the murine α1 (I) collagen locus" *Science*, vol. 259, pp. 1904–1907 (1993).

Tagle et al., "Magnetic bead capture of expressed sequences encoded with large genomic segments" *Nature*, 361:751–753 (1993).

The European Polycystic Kidney Disease Consortium, The polycystic kidney disease 1 gene encodes a 14 kb transcript and lies within a duplicated region on chromosome 16" *Cell*, 77:881–894 (1994).

The Huntington's Disease Collaborative Research Group, "A novel gene containing a trinucleotide repeat that is expanded and unstable on Huntington's disease chromosomes" *Cell*, 72:971–983 (1993).

Trofatter et al., "A novel moesin-, ezrin-, radixin-like gene is a candidate for the neurofibromatosis 2 tumor suppressor" *Cell*, 72:791–800 (1993).

Vanagaite et al., "Physical localization of microsatellite markers at the ataxia–telangiectasia locus at 11q22–q23" *Genomics*, 22:231–233 (1994a).

Vanagaite et al., "A high-density microsatellite map of the ataxia–telangiectasia locus" *Hum. Genet.*, 95:451–454 (1995).

Vetrie et al., "The gene involved in X-linked agammaglobulinaemia is a member of the src family of protein-tyrosine kinases" *Nature*, 361:226–233 (1993).

Wagner et al., "Gene transfer into murine stem cells and mice using retroviral vectors" in *Gene Transfer into Mice*, pp. 691–700.

Weber and May, "Abundant class of human DNA polymorphisms which can by typed using the polymerase chain reaction" *Am. J. Hum. Genet.*, 44:388–396 (1989).

Ziv et al., "Ataxia–telangiectasia: linkage analysis in highly inbred Arab and Druze families and differentiation . . . " *Hum. Genet.*, 88:619–626 (1992).

Ziv et al., "The ATC (ataxia–telangiectasia complementation group C) locus localizes to 11q22–q23" *Genomics*, 9:373–375 (1991).

Rasio et al, Cancer Research 55 (24), 6053–6057, Dec. 1995.

Kapp, "Cloning of a candidate gene for Ataxia–Telangiectasia Group D" *Am. J. Hum. Genet.*, 51:45–54 (1992).

Leonardt et al., "Nucleotide sequence analysis of a candidate gene for Ataxia–Telangiectasia Group D (ATDC)" *Genomics*, 19:130–136 (1994).

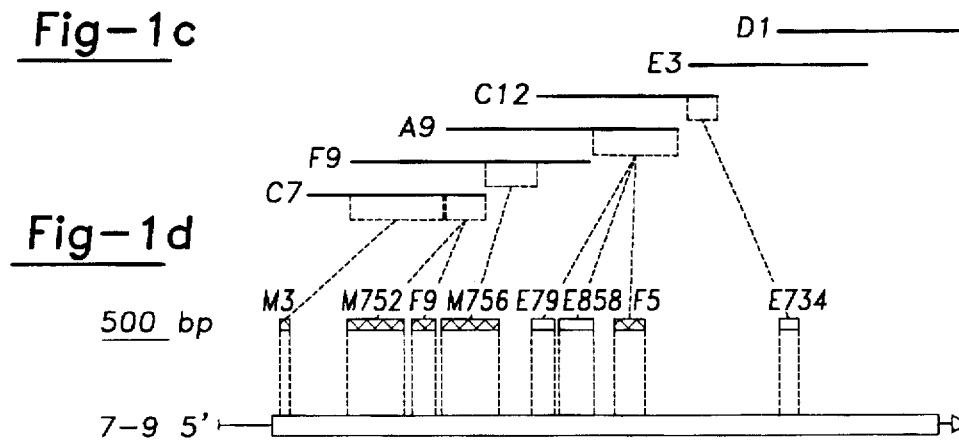

MUTATED PROTEINS ASSOCIATED WITH ATAXIA-TELANGIECTASIA

This application is a Continuation-In-Part of U.S. Ser. No. 08/441,822, filed May 16, 1995.

GRANT SUPPORT

This work was supported in part by grants from the National Institutes of Health, United States-Israel Binational Science Foundation, A-T Medical Research Foundation, A-T Medical Trust, and the A-T Children's Project.

TECHNICAL FIELD

The present invention relates to the determination of the gene sequence, mutations of which cause ataxia-telangiectasia (A-T), designated ATM, and the use of the gene and gene products in detection of carriers of the A-T gene, and preparing native and transgenic organisms in which the gene products encoded by the ATM gene or its homolog in other species are artificially produced, or the expression of the native ATM gene is modified.

BACKGROUND OF THE INVENTION

Ataxia-telangiectasia (A-T) is a progressive genetic, disorder affecting the central nervous and immune systems, and involving chromosomal instability, cancer predisposition, radiation sensitivity, and cell cycle abnormalities. Studies of the cellular phenotype of A-T have pointed to a defect in a putative system that processes a specific type of DNA damage and initiates a signal transduction pathway controlling replication and repair. For a general review of Ataxia-telangiectasia, reference is hereby made to the review *Ataxia-Telangiectasis: Closer to Unraveling the Mystery*, Eur. J. Hum. Genet. (Shiloh, 1995) which, along with its cited references, is hereby incorporated by reference.

Despite extensive investigation over the last two decades, A-T has remained a clinical and molecular enigma. A-T is a multi-system disease inherited in an autosomal recessive manner, with a worldwide frequency of 1:100,000 live births and an estimated carrier frequency of 1% in the American population. Notable concentrations of A-T patients outside the United States are in Turkey, Italy and Israel. Israeli A-T patients are Moroccan Jews, Palestinian Arabs, Bedouins and Druzes.

Cerebellar ataxia that gradually develops into general motor dysfunction is the first clinical hallmark and results from progressive loss of Purkinje cells in the cerebellum. Oculocutaneous telangiectasia (dilation of blood vessels) develops in the bulbar conjunctiva and facial skin, and is later accompanied by graying of the hair and atrophic changes in the skin. Somatic growth is retarded in most patients, and ovarian dysgenesis is typical for female patients. Among occasional endocrine abnormalities, insulin-resistant diabetes is predominant, and serum levels of alpha-fetoprotein and carcinoembryonic antigen are elevated. The thymus is either absent or vestigial, and other immunological defects include reduced levels of serum IgA, IgE or IgG2, peripheral lymphopenia, and reduced responses to viral antigens and allogeneic cells, that cause many patients to suffer from recurrent sinopulmonary infections.

Cancer predisposition in A-T is striking: 38% of patients develop malignancies, mainly lymphoreticular neoplasms and leukemias. But, A-T patients manifest acute radiosensitivity and must be treated with reduced radiation doses, and not with radiomimetic chemotherapy. The most common cause of death in A-T, typically during the second or third decade of life, is sinopulmonary infections with or without malignancy.

The complexity of the disease is reflected also in the cellular phenotype. Chromosomal instability is expressed as increased chromosomal breakage and the appearance in lymphocytes of clonal translocations specifically involving the loci of the immune system genes. Such clones may later become predominant when a lymphoreticular malignancy appears. Primary fibroblast lines from A-T patients show accelerated senescence, increased demand for certain growth factors, and defective cytoskeletal structure. Most notable is the abnormal response of A-T cells to ionizing radiation and certain radiomimetic chemicals. While hypersensitive to the cytotoxic and clastogenic effects of these agents, DNA synthesis is inhibited by these agents to a lesser extent than in normal cells. The concomitant lack of radiation-induced cell cycle delay and reduction of radiation-induced elevation of p53 protein are evidence of a defect in a cell cycle checkpoint. Increased intrachromosomal recombination in A-T cells was also noted recently.

Prenatal diagnoses of A-T using cytogenetic analysis or measurements of DNA synthesis have been reported, but these tests are laborious and subject to background fluctuations and, therefore, not widely used.

A-T homozygotes have two defective copies of the A-T gene and are affected with the disease. A-T heterozygotes (carriers) have one normal copy of the gene and one defective copy of the gene and are generally healthy. When two carriers have children, there is a 25% risk in every pregnancy of giving birth to an A-T affected child.

A-T heterozygotes show a significant excess of various malignancies, with an 3 to 4-fold increased risk for all cancers between the ages of 20 and 80, and a 5-fold increased risk of breast cancer in women. These observations turn A-T into a public health problem and add an important dimension to A-T research, particularly to heterozygote identification. Cultured cells from A-T heterozygotes indeed show an intermediate degree of X-ray sensitivity, but the difference from normal cells is not always large enough to warrant using this criterion as a laboratory assay for carrier detection. Cytogenetic assays are labor intensive and not always consistent. The main reason for the unreliability of the previous assay methods is due to various degrees in overlap between A-T heterozygotes and non-heterozygotes with respect to radiosensitivity.

The nature of the protein missing in A-T is unknown. Cell fusion studies have established four complementation groups in A-T, designated A, C, D and E, suggesting the probable involvement of at least four genes or four types of mutations in one gene, with inter-allelic-complementation. These four groups are clinically indistinguishable and were found to account for 55%, 28%, 14% and 3% of some 80 patients typed to date. In Israel, several Moroccan Jewish patients were assigned to group C, while Palestinian Arab patients were assigned to group A.

The general chromosomal localization of the putative A-T gene(s) has been determined, but not the sequence. An A-T locus containing the A-T(A) mutations was localized by Gatti et al. (1988) to chromosome 11, region q22-23, using linkage analysis. The A-T(C) locus was localized by applicants to the same region of chromosome 11, region q22-23, by linkage analysis of an extended Jewish Moroccan A-T family (Ziv et al., 1991). Further studies, conducted by an international consortium in which applicant participated (McConville et al., 1990; Foroud et al., 1991; Ziv et al., 1992), reconfirmed this localization in a series of studies and gradually narrowed the A-T locus to an interval estimated at 4 centimorgan, which probably contains also the A-T(E) mutations.

A proposed gene for complementation group D is disclosed in U.S. Pat. No. 5,395,767 to Murnane et al., issued Mar. 7, 1995. This sequence was found not to be mutated in any complementation group of A-T. Further, the gene sequence was mapped physically distant from the presumptive A-T locus.

Therefore, in order to better understand the nature and effects of A-T, as well as to more accurately and consistently determine those individuals who may carry the defective gene for A-T, it would be advantageous to isolate and determine the gene sequence, mutations of which are responsible for causing A-T, and utilize this sequence as a basis for detecting carriers of A-T and thereby be able to more beneficially manage the underlying conditions and predispositions of those carriers of the defective gene.

SUMMARY OF THE INVENTION AND ADVANTAGES

According to the present invention, a gene sequence and mutations of this sequence which cause ataxia-telangiectasia (A-T), designated ATM, has been purified, isolated and determined.

The present invention further includes the method for identifying carriers of the defective A-T gene and defective A-T gene products.

Further, the present invention provides transgenic and knockout nonhuman and animal and cellular models.

The role of the ATM gene in cancer predisposition makes this gene an important target for screening. The detection of A-T mutation carriers is particularly significant in light of their radiation-sensitivity so that carrier exposure to radiation can be properly monitored and avoided.

BRIEF DESCRIPTION OF THE DRAWINGS

Other advantages of the present invention will be readily appreciated as the same becomes better understood by reference to the following detailed description when considered in connection with the accompanying drawings wherein:

FIGS. 1A–E illustrate the positional cloning steps to identify the A-T gene(s) wherein FIG. 1A is a high-density marker map of the A-T region on chromosome 11q22-23 (Vanagaite et al., 1995), constructed by generating microsatellite markers within genomic contigs spanning the region and by physical mapping of available markers using the same contigs, the prefix "D11" has been omitted from the marker designations, FDX: the adrenal ferredoxin gene, ACAT: the acetoacetyl-coenzyme A thiolase gene, the stippled box denotes the A-T interval, defined recently by individual recombinants between the markers S1818 and S1819 in a consortium linkage study (Lange et al., 1995), the solid box indicates the two-lod confidence interval for A-T obtained in that study, between S1294 and S384;

FIG. 1B illustrates a part of a YAC contig constructed across this region (Rotman et al., 1994c);

FIG. 1C illustrates part of a cosmid contig-spanning the s384–S1818 interval, generated by screening a chromosome-11 specific cosmid library with YAC clones Y16 and Y67, and subsequent contig assembly of the cosmid clones by physical mapping (Shiloh, 1995);

FIG. 1D illustrates products of gene hunting experiments wherein solid boxes denote cDNA fragments obtained by using cosmid and YAC clones for hybrid selection of cDNAs (Lovett et al. 1991; Tagle et al., 1993) from a variety of tissues, open boxes denote putative exons isolated from these cosmids by exon trapping (Church et al., 1993), these sequences hybridized back to specific cosmids (broken lines), which allowed their physical localization to specific subregions of the contig (dotted frames); and FIG. 1E illustrates a 5.9 kb cDNA clone, designated 7-9, identified in a fibroblast cDNA library using the cDNA fragments and exons in 1D as a probe wherein the open box denotes an open reading frame of 5124 nucleotides, solid lines denote untranslated regions, striped arrowheads denote two Alu elements at the 3' end, and wherein dotted lines drawn between cDNA fragments and exons the cDNA indicate colinearity of sequences.

DETAILED DESCRIPTION OF THE PREFERRED EMBODIMENT

The present invention consists of a purified, isolated and cloned nucleic acid sequence encoding a gene, designated ATM, mutations in which cause ataxia-telangiectasia and genetic polymorphisms thereof. The nucleic acid can be isolated genomic DNA, cDNA or mRNA. A partial sequence of the ATM gene is set forth in SEQ ID No:1 and in SEQ ID No:3.

SEQ ID No:1 includes and extends the cDNA sequence of clone 7-9 in the 5' direction as described herein below. Cosmid clones containing the entire 7-9 sequence are described in Savitsky et al. (1995) and incorporated herein by reference.

SEQ ID No:3 is a 6.5 Kb cloned DNA sequence, designated A-T/4 and represents a sequence of DNA which extends the length of SEQ ID No:1 in the 3' direction. SEQ ID No:3 begins at nucleotide 1432 of SEQ ID No:1 and is identical to SEQ ID No:1 through nucleotide 6556 of SEQ ID No:1 which corresponds to nucleotide 5246 of SEQ ID No:3. From nucleotide 5247 of SEQ ID No:3 through its last nucleotide, SEQ ID No:3 differs from SEQ ID No:1. This difference is thought to reflect alternative splicing creating different protein isoforms.

Polymorphisms are variants in the sequence generally found between different ethnic and geographic locations which, while having a different sequence, produce functionally equivalent gene products.

Current mutation data (as shown in Table 1) indicate that A-T is a disease characterized by considerable allelic heterogenicity. It would not be surprising if there were hundreds (or even thousands) of ATM mutations (as is the case for cystic fibrosis and BRACAI). Mutations imparting defects into the A-T gene can be point mutations, deletions, insertions or rearrangements. The mutations can be present within the nucleotide sequence of the either or both alleles of the ATM gene such that the resulting amino acid sequence of the ATM protein product is altered in one or both copies of the gene product imparting ataxia-telangiectasia. Alternatively, a mutation event selected from the group consisting of point mutations, deletions, insertions and rearrangements could have occurred within the flanking sequences and/or regulatory sequences of ATM such that regulation of ATM is altered imparting ataxia-telangiectasia.

Table 1 illustrates several mutations in the ATM gene found in A-T patients. Mutations in the ATM gene were found in all of the complementation groups suggesting that ATM is the sole gene responsible for all A-T cases.

TABLE 1 illustrates several mutations found in A-T patients

| Patient[1] | Ethnic/ geographic origin | Complementation group[4] | Mutation mRNA sequence change | Protein alteration | Codon[9] | Patient's genotype[10] |
|---|---|---|---|---|---|---|
| AT2RO | Arab | A | Deletion of 11 nt[5] | Frameshift, truncation | 499 | Homozygote |
| AT3NG | Dutch | A | Deletion of 3 nt | Deletion, 1 residue[8] | 1512 | Compound heterozygote |
| AT15LA | Philippine | A | Insertion, +A | Frameshift, truncation | 557 | Compound heterozygote |
| AT3LA[2] | African-American | C | Deletion of 139 nt[6]/ | Frameshift, trunction | 1196 | Compound heterozygotes |
| AT4LA[2] | | | Deletion of 298 nt[6] | | | |
| AT2BR | Celtic/Irish | C | Deletion, 9 nt | Deletion, 3 residues | 1198–1200 | Homozygote |
| AT1ABR | Australian | E | Deletion, 9 nt | Deletion, 3 residues | 1198–1200 | Homozygote |
| AT2ABR | (Irish/British) | | | | | |
| AT5BI[2] | Indian/English | D | Deletion, 6 nt | Deletion, 2 residues | 1079–1080 | Compound heterozygotes |
| AT6BI[2] | | | | | | |
| F-2079[3] | Turkish | ND | Insertion, +C[5] | Frameshift, truncation | 504 | Homozygote |
| AT29RM | Italian | ND | Deletion of 175 nt | Frameshift, truncation | 132 | Homozygote |
| AT103LO | Canadian | ND | Insertion, +A | Frameshift, truncation | 1635 | Homozygote |
| F-596[3] | Palestinian Arab | ND | Deletion[7] | Truncation | Most of ORF | Homozygote |

[1]Cell line designation.
[2]Sibling patients in both of whom the same mutation was identified.
[3]Patient expected to be homozygous by descent for an A-T mutation.
[4]According to the methods of Jaspers et al. (1988)
ND: not determined.
[5]An identical sequence change was observed in genomic DNA
[6]No evidence for deletion was observed in genomic DNA. In both siblings, a normal mRNA was observed in addition to the two deleted species. The two deleted mRNAS may represent abnormal splicing events caused by a splice site mutation.
[7]Reflects a genomic deletion segregating with the disease in Family N.
[8]The deleted serine residue is located within the P13-kinase signature sequence (1507–1527 of SEQ ID No:2).
[9]Numbers refer to residue positions in SEQ ID No:2.
[10]In all the compound heterozygotes, the second mutation is still unidentified.

In cloning the gene for A-T, the strategy used was a common strategy in identifying a disease gene with an unknown protein product known as positional cloning, as is well known in the art. In positional cloning, the target gene is localized to a specific chromosomal region by establishing linkage between the disease and random genetic markers defined by DNA polymorphisms. Definition of the smallest search interval for the gene by genetic analysis is followed by long-range genomic cloning and identification of transcribed sequences within the interval. The disease gene is then identified among these sequences, mainly by searching for mutations in patients.

Several important and long sought disease genes were isolated recently in this way (Collins, 1992; Attree et al., 1992; Berger et al., 1992; Chelly et al., 1993; Vetrie et al., 1993; Trofatter et al., 1993; The Huntington's Disease Collaborative Research Group, 1993; The European Polycystic Kidney Disease Consortium, 1994; Miki et al., 1994).

Two complementary methods were used for the identification of transcribed sequences (gene hunting): hybrid selection based on direct hybridization of genomic DNA with cDNAs from various sources (Parimoo et al., 1991; Lovett et al., 1991); and exon trapping (.also called exon amplification), which identifies putative exons in genomic DNA by virtue of their splicing capacity (Church et al., 1993). In hybrid selection experiments, cosmid and YAC clones served to capture cross-hybridizing sequences in cDNA collections from placenta, thymus and fetal brain, using the magnetic bead capture protocol (Morgan et al., 1992; Tagle et al., 1993). In parallel experiments, YAC clones were bound to a solid matrix and used to select cDNA fragments from a heterogeneous cDNA collection representing several human tissues (Parimoo et al., 1993). The cosmids were also used for exon trapping with the pSPL3 vector (Church et al., 1994). The captured cDNA fragments and trapped exons were mapped back to the A-T region by hybridization to several radiation hybrids containing various portions of the 11q22-23 region (Richard et al., 1993; James et al., 1994), and to high-density grids containing all the YACs and cosmids spanning this interval. An extensive transcriptional map of the A-T region was thus constructed (Shiloh et al., 1994).

Pools of adjacent cDNA fragments and exons, expected to converge into the same transcriptional units, were used to screen cDNA libraries. A cluster of 5 cDNA fragments and 3 exons mapped in close proximity to the marker D11S535, where the location score for A-T had peaked (Lange et al., 1995). All these sequences hybridized to the same 5.9 kb of the cDNA clone, 7-9, obtained from a fibroblast cDNA library.

Hybridization of the 7-9 cDNA clone to the radiation hybrid panel indicated that the entire transcript was derived form the chromosome 11 locus. The full sequence of this clone was obtained using a shotgun strategy, and found to contain 5921 bp which includes an open reading frame (ORF) of 5124 nucleotides, a 538 bp 3' untranslated region (3' UTR), and a 259 bp 5' non-coding sequence containing stop codons in all reading frames. (Genbank Accession No. U26455). Two Alu repetitive elements were observed at the 3' end of this clone and in nine smaller clones representing this gene from the same cDNA library. Since no polyadenylation signal was identified in these cDNA clones, their poly(A) tracts were assumed to be associated with the Alu element rather than being authentic poly(A) tails of these transcripts. This assumption was later supported when applicants identified a cDNA clone derived from the same gene in a leukocyte cDNA library, with an alternative 3' UTR containing a typical polyadenylation signal. Alignment of the cDNA with the genomic physical map showed that the corresponding gene is transcribed from centromere to telomere.

Hybridization of a probe containing the entire ORF of clone 7-9 to northern blots from various tissues and cell lines revealed a major transcript of 12 kb in all tissues and cell types examined, and minor species of various sizes in several tissues, possibly representing alternatively spliced transcripts of the corresponding gene or other homologous sequences. Analysis of 12 additional cDNA clones corresponding to this gene indicated a plethora of transcripts generated by multiple alternative splicing combinations. Genomic sequencing later identified the 5' non-coding region of clone 7-9 as sequences of the unspliced adjacent intron. Two other cDNA clones from a leukocyte cDNA library were found to contain this intronic sequence in their 5' ends. These clones may represent either splicing intermediates, or alternatively spliced transcripts of this gene, in which sequences of the adjacent intron were left to serve as an untranslated leader.

The invention further provides a purified protein as encoded by the ATM gene and analogs thereof. A consensus sequence is set forth in SEQ ID No:2. The present invention further provides for mutations in SEQ ID No:2 which cause ataxia-telangiectasia, for example, as set forth in Table 1.

An analog will be generally at least 70% homologous over any-portion that is functionally relevant. In more preferred embodiments, the homology will be at least 80% and can approach 95% homology to the ATM protein. The amino acid sequence of an analog may differ from that of the ATM protein when at least one residue is deleted, inserted or substituted but the protein remains functional and does not cause A-T. Differences in glycosylation can provide analogs.

The present invention provides an antibody, either polyclonal or monoclonal, which specifically binds to a polypeptide/protein encoded by the ATM gene. In preparing the antibody, either the entire protein (with and without mutations), the consensus protein set forth in SEQ ID No:2, peptide amino acid sequences isolated from the amino acid sequence as set forth in SEQ ID No:2 or mutant peptide sequences can be used as an immunogen.

The present invention specifically provides antibodies against the following peptides:

HEPANSSASQSTDLC (SEQ ID No:4),
CKRNLSDIDQSFDKV (SEQ ID No:5),
PEDETELHPTLNADDQEC (SEQ ID No:6), and
CKSLASFIKKPFDRGEVESMEDDTNG (SEQ ID No:7).

The antibodies may be either monoclonal or polyclonal. Conveniently, the antibodies may be prepared against a synthetic peptide based on the sequence, or prepared recombinantly by cloning techniques or the natural gene product and/or portions thereof may be isolated and used as the immunogen. Such proteins or peptides can be used to produce antibodies by standard antibody production technology well known to those skilled in the art as described generally in Harlow and Lane, *Antibodies: A Laboratory Manual*, Cold Spring Harbor Laboratory Press, Cold Spring Harbor, N.Y., 1988.

For producing polyclonal antibodies a host, such as a rabbit or goat, is immunized with the protein or peptide, generally with an adjuvant and, if necessary, coupled to a carrier; antibodies to the protein are collected from the sera.

For producing monoclonal antibodies, the technique involves hyperimmunization of an appropriate donor, generally a mouse, with the protein or peptide fragment and isolation of splenic antibody producing cells. These cells are fused to a cell having immortality, such as a myeloma cell, to provide a fused cell hybrid which has immortality and secretes the required antibody. The cells are then cultured, in bulk, and the monoclonal antibodies harvested from the culture media for use.

The antibody can be bound to a solid support substrate or conjugated with a detectable moiety or be both bound and conjugated as is well known in the art. (For a general discussion of conjugation of fluorescent or enzymatic moieties see Johnstone and Thorpe, *Immunochemistry in Practice*, Blackwell Scientific Publications, Oxford, 1982.) The binding of antibodies to a solid support substrate is also well known in the art. (see for a general discussion Harlow and Lane *Antibodies: A Laboratory Manual*, Cold Spring Harbor Laboratory Publications, N.Y. 1988) The detectable moieties contemplated with the present invention can include, but are not limited to, fluorescent, metallic, enzymatic and radioactive markers such as biotin, gold, ferritin, alkaline phosphatase, β-galactosidase, peroxidase, urease, fluorescein, rhodamine, tritium, $^{14}C$ and iodination.

The present invention provides vectors comprising an expression control sequence operatively linked to the nucleic acid sequence of the ATM gene, SEQ ID No:1, SEQ ID No:3 and portions thereof as well as mutant sequences which lead to the expression of A-T. The present invention further provides host cells, selected from suitable eucaryotic and procaryotic cells, which are transformed with these vectors.

The present invention provides for transgenic ATM gene and mutant ATM gene animal and cellular (cell lines) models as well as for knockout ATM models. The transgenic models include those carrying, at least, SEQ ID NO:1 and/or SEQ ID No:3. These models are constructed using standard methods known in the art and as set forth in U.S. Pat. Nos. 5,387,742, 5,360,735, 5,347,075, 5,298,422, 5,288,846, 5,221,778, 5,175,385, 5,175,384, 5,175,383, 4,736,866 as well as Burke and Olson, (1991), Capecchi, (1989), Davies et al., (1992), Dickinson et al., (1993), Huxley et al., (1991), Jakobovits et al., (1993), Lamb et al., (1993), Rothstein, (1991), Schedl et al., (1993), Strauss et al., (1993), Further, patent applications WO 94/23049, WO 93/14200, WO 94/06908, WO 94/28123 also provide information.

The present invention provides methods for detecting carriers of the defective gene and gene products which cause ataxia-telangiectasia and/or detecting normal copies of the ATM gene and its gene product. The methods comprise the steps of obtaining a sample from a test subject, isolating the appropriate test material from the sample and assaying for the target nucleic acid sequence or gene product. The sample can be tissue or bodily fluids from which genetic material and/or proteins are isolated using methods standard in the art. For example, DNA can be isolated from lymphocytes, cells in amniotic fluid and chorionic villi (Llerena et al., 1989).

The specimen can be assayed for polypeptides/proteins by immunohistochemical and immunocytochemical staining (see generally Stites and Terr, *Basic and Clinical Immunology*, Appleton and Lange, 1994), ELISA, RIA, immunoblots, Western blotting, immunoprecipitation, functional assays and protein truncation test. In preferred embodiments, Western blotting, functional assays and protein truncation test (Hogervorst et al., 1995) will be used. mRNA complementary to the target nucleic acid sequence can be assayed by in situ hybridization, Northern blotting and reverse transcriptase -polymerase chain reaction. Nucleic acid sequences can be identified by in situ hybridization, Southern blotting, single strand conformational polymorphism, PCR amplification and DNA-chip analysis using specific primers. (Kawasaki, 1990; Sambrook, 1992; Lichter, et al, 1990; Orita et al, 1989; Fodor et al., 1993; Pease et al., 1994)

ELISA assays are well known to those skilled in the art. Both polyclonal and monoclonal antibodies can be used in the assays. Where appropriate other immunoassays, such as radioimmunoassays (RIA) can be used as are known to those in the art. Available immunoassays are extensively described in the patent and scientific literature. See, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521 as well as Sambrook et al, 1992.

Current mutation data (as shown in Table 1) indicate that A-T is a disease characterized by considerable allelic heterogenicity. It would not be surprising if there were hundreds (or even thousands) of ATM mutations (as is the case for cystic fibrosis and BRACAI). Thus, it will be important for a successful mutation screen to be able to detect all possible nucleotide alterations in the ATM gene, rather than being focused on a limited subset. Methods including direct sequencing of PCR amplified DNA or RNA or DNA chip hybridization (Fodor et al., 1993; Pease et al., 1994) can be applied along with other suitable methods known to those skilled in the art.

Functional assays can be used for detection of A-T carriers or affected individuals. For example, if the ATM protein product is shown to have PI 3-kinase biochemical activity which can be assayed in an accessible biological material, such as serum, peripheral leukocytes, etc., then homozygous normal individuals would have approximately normal biological activity and serves as the positive control. A-T carriers would have substantially less than normal biological activity, and affected (i.e. homozygous) individuals would have even less biological activity and serving as a negative control. Such a biochemical assay currently serves as the basis for Tay-Sachs carrier detection.

Materials and Method

General Methods in Molecular Biology

Standard molecular biology techniques known in the art and not specifically described were generally followed as in Sambrook et al., *Molecular Cloning: A Laboratory Manual*, Cold Springs Harbor Laboratory, N.Y. (1989, 1992), and in Ausubel et al., *Current Protocols in Molecular Biology*, John Wiley and Sons, Baltimore, Md. (1989).

Patient and family resources: A cell line repository was established containing to 230 patient cell lines and 143 cell lines from healthy members of Moroccan Jewish, Palestinian Arab and Druze families. Some of these pedigrees are highly inbred and unusually large (Ziv et al., 1991; Ziv, 1992). In view of the large number of meiotic events required for high-resolution linkage analysis, applicants Collaborated with Dr. Camel McConville (University of Birmingham, UK) and Dr. Richard Gatti (UCLA, Los Angeles, Calif.), who established extensive repositories of A-T families. Linkage analysis was conducted on a pool of 176 families.

Definition of the A-T interval by genetic analysis: Studies based only on analysis of Israeli A-T families enabled localization of the A-T(C) gene at 11q22-23 (Ziv, 1991), and confirmed the localization of A-T(A) mutation in Palestinians to the same region (Ziv et al., 1992). Studies with the Birmingham group further narrowed the major A-T interval to 4 centimorgans, between D11S611 and D11S1897 (McConville et al., 1993), and subsequently to 3 centimorgans, between GRIA4 and D11S1897 (Ambrose et al., 1994; McConville et al., 1994) (see also Shiloh, 1995, and FIG. 1).

All these studies were conducted with biallelic markers, whose power is limited by their low polymorphic information content (PIC). The recently discovered microsatellite markers based on variable numbers of tandem simple repeats (Litt and Luty, 1989; Weber and May, 1989) are much more powerful due to their high degree of polymorphism. Microsatellite markers were used to saturate the A-T region using two approaches. The first, was based on physical mapping of microsatellite markers generated by others which were loosely linked to chromosome 11q.

Mapping experiments were conducted using YAC and cosmid contigs which allowed precise, high-resolution localization of DNA sequences in this region of chromosome 11. These experiments led to the localization of 12 microsatellites at the A-T region (Vanagaite et al., 1994a; Vanagaite et al., 1995).

The second approach was based on generating new microsatellites within the YAC contig. A rapid method for the identification of polymorphic CA-repeats in YAC clones was set up (Rotman, 1995) resulting in the generation of twelve new markers within the A-T locus (Vanagaite et al., 1995; Rotman et al., 1995; Rotman et al., 1994b). Hence, the high-density microsatellite map constructed in this manner contained a total of 24 new microsatellite markers and spans the A-T locus and flanking sequences, over a total of six megabases (Vanagaite et al., 1995).

Repeated linkage analysis on the entire cohort of A-T families indicated that the A-T(A) locus was definitely located within a 1.5 megabase region between D11S1819 and D11S1818 (Gatti et al., 1994) as shown in FIG. 1 and in Shiloh (1995), with a clear peak of the cumulative lod score under D11S535 (Lange et al., 1994).

Concomitant with these studies, linkage disequilibrium (LD) analysis of Moroccan-Jewish A-T patients was conducted. LD refers to the non-random association between alleles at two or more polymorphic loci (Chakravarti et al., 1984). LD between disease loci and linked markers was a useful tool for the fine localization of disease genes (Chakravarti et al., 1984; Kerem, et al. 1989; Ozelius et al., 1992; Sirugo et al., 1992; Hastbacka et al., 1992; Mitchison et al., 1993). LD is particularly powerful in isolated ethnic groups, where the number of different mutations at a disease locus is likely to be low (Hastbacka et al., 1992; Lehesjoki et al., 1993; Aksentijevitch et al., 1993). Early on, applicants observed very significant LD ($p<0.02$-$p<0.001$) between A-T and markers along the D11S1817-D11S927 region in the patients of the sixteen Moroccan-Jewish A-T families identified in Israel (Oskato et al., 1993). Further analysis with the new markers narrowed the peak of linkage disequilibrium to the D11S384-D11S1818 region as shown in FIG. 1.

Haplotype analysis indicated that all of the mutant chromosomes carry the same D11S384-D11S1818 haplotype, suggesting a founder effect for A-T in this community, with one mutation predominating.

Long-range cloning of the A-T(A)/A-T(C) region: Cloning the disease locus in a contig (set of overlapping clones) was essential in isolating the A-T disease gene. The entire ALT locus and flanking region in a contig of yeast artificial chromosomes (YACs) was cloned by methods well known in the art (Rotman et al. 1994c; Rotman et al., 1994d). This contig was instrumental in the construction of the microsatellite map of the region (Vanagaite et al., 1995) and subsequently enabled construction of cosmid contigs extending over most of the interval D11S384-D11S1818. Cosmids corresponding to the YAC clones were identified in a chromosome 11-specific cosmid library supplied by Dr. L. Deaven (Los Alamos National Laboratory) and were ordered into contigs by identifying overlaps as shown in FIG. 1.

Isolation of the A-T gene: Transcribed sequences were systematically identified based on two complementary methods:

1. Use of an improved direct selection method based on magnetic bead capture (MBC) of cDNAs corresponding to genomic clones (Morgan et al., 1992; Tagle, et al., 1993). In several, large-scale experiments YAC or cosmid DNA was biotinylated and hybridized to PCR-amplified cDNA from thymus, brain and placenta. Genomic DNA-cDNA complexes were captured using streptavidin-coated magnetic beads which was followed with subsequent elution, amplification, and cloning of captured cDNAs. The cDNA inserts were excised from a gel, self-ligated to form concatamers and sonicated to obtain random fragments. These fragments were size fractionated by gel electrophoresis, and the 1.0-1.5 Kb fraction was extracted from the gel and subcloned in a plasmid vector. The end portions of individual clones were sequenced using vector-specific primers, in an automated sequencer (Model 373A, Applied Biosystems), and the sequences were aligned using the AutoAssembler program (Applied Biosystems Division, Perkin-Elmer Corporation). In the final sequence each nucleotide position represents at least 3 independent overlapping readings.

YACs were also used and were no less efficient than cosmids as starting material for MBC, with more than 50% of the products mapping back to the genomic clones. However, when a small panel of radiation hybrids spanning the A-T region was used to test the cDNA fragments, it was found that some clones that hybridized back to the YACs and cosmids were not derived from this region. This pitfall probably stems from limited homology between certain portions of different genes, and points up the necessity to use radiation hybrid mapping when testing the authenticity of the captured sequences, and not to rely solely on cloned DNA for this purpose.

Homology searches in sequence databases showed that only one of the first 105 cDNA fragments mapped to the A-T region was homologous to a sequence previously deposited in one of the databases, as an expressed sequence tag (EST).

2. Exon amplification, also termed "exon trapping" (Duyk et al., 1990; Buckler et al., 1991), is based on cloning genomic fragments into a vector in which exon splice sites are flagged by splicing to their counterpart sites in the vector. This method of gene identification was expected to complement the MBC strategy, since it does not depend on the constitution of cDNA libraries or on the relative abundance of transcripts, and is not affected by the presence of repetitive sequences in the genomic clones. An improved version of this system (Church et al., 1993) that eliminated problems identified in an earlier version, including a high percentage of false positives and the effect of cryptic splice sites was utilized. Each experiment ran a pool of three to five cosmids with an average of two to five exons identified per cosmid. A total of forty five exons were identified.

Sequence analysis and physical mapping indicated that MBC and exon amplification were complementary in identifying transcribed sequences.

The availability of a deep cosmid contig enabled rapid and precise physical localization of the CDNA fragments and captured exons, leading to a detailed transcriptional map of the A-T region.

Both MBC and exon amplification yielded short (100–1000 bp) transcribed sequences. Those sequences were used as anchor points in isolating full-length clones from twenty eight cDNA libraries currently at applicants disposal and which represented a variety of tissues and cell lines.

Initial screening of the cDNA libraries by polymerase chain reaction (PCR) using primer sets derived from individual cDNA fragments or exons aided in the identification of the libraries most likely to yield corresponding cDNA clones.

Large scale screening experiments were carried out in which most of the cDNA fragments and exons were used in large pools. In addition to the mass screening by hybridization, PCR-based screening methods and RACE (rapid amplification of cDNA ends) (Frohman et al., 1988; Frohman et al., 1994) was employed to identify full-length cDNAs.

The above experiments resulted in the identification and isolation of a cDNA clone designated 7-9 the sequence of which is included in SEQ ID No:1 and which is derived from a gene located under the peak of cumulative location score obtained by linkage analysis as shown in FIG. 1. The gene extends some 300 kilobases (kb) of genomic DNA and codes for two major mRNA species of 12 kb and 10.5 kb in length. The 7-9 clone is 5.9 kb in length and, therefore, is not a full length clone.

An open reading frame of 5124 bp within this cDNA encodes a protein with signature motifs typical of signal transduction proteins, most notably, phosphatidylinositol 3-kinases (PI 3-kinases). PI 3-kinases take part in the complex system responsible for transmitting signals from the outer environment of a cell into the cell. To date, it is not clear whether the protein produced from the 7-9 clone is a part of this transduction system or if it merely contains sequence motifs typical to signal transduction proteins.

The present invention further includes a recombinant protein encoded by the 7-9 clone. This recombinant protein is isolated and purified by techniques known to those skilled in the art.

Using the present invention, it is possible to transform host cells, including *E. coli*, using the appropriate vectors so that they carry either the native or recombinant DNA sequence of the 7-9 cDNA clone or a mutated sequence containing point mutations, deletions, insertions, or rearrangements of DNA. Such transformed cells allow the study of the function and the regulation of the A-T gene. In particular, use of recombinantly transformed host cells allows for the study of the mechanisms of A-T, in particular, it will allow for the study of gene function interrupted by the mutations in the A-T gene region.

Vectors are known or can be constructed by those skilled in the art and should contain all expression elements necessary to achieve the desired transcription of the sequences. Other beneficial characteristics can also be contained within the vectors such as mechanisms for recovery of the nucleic acids in a different form. Phagemids are a specific example of such beneficial vectors because they can be used either as plasmids or as bacteriophage vectors. Examples of other vectors include viruses such as bacteriophages, baculoviruses and retroviruses, DNA viruses, cosmids, plasmids, liposomes and other recombination vectors. The vectors can also contain elements for use in either procaryotic or eucaryotic host systems. One of ordinary skill in the art will know which host systems are compatible with a particular vector.

The vectors can be introduced into cells or tissues by any one of a variety of known methods within the art. Such methods can be found generally described in Sambrook et al., *Molecular Cloning: A Laboratory Manual*, Cold Springs Harbor Laboratory, N.Y. (1992), in Ausubel et al., *Current Protocols in Molecular Biology*, John Wiley and Sons, Baltimore, Md. (1989), Chang et al., *Somatic Gene Therapy*, CRC Press, Ann Arbor, Mich. (1995), Vega et al., Gene Targeting, CRC Press, Ann Arbor, Mich. (1995) and Gilboa, et al (1986) and include, for example, stable or transient transfection, lipofection, electroporation and infection with recombinant viral vectors. Introduction of nucleic acids by infection offers several advantages over the other listed methods. Higher efficiency can be obtained due to their infectious nature. Moreover, viruses are very specialized and typically infect and propagate in specific cell types. Thus, their natural specificity can be used to target the vectors to specific cell types in vivo or within a tissue or mixed culture of cells. Viral vectors can also be modified with specific receptors or ligands to alter target specificity through receptor mediated events.

Recombinant methods known in the art can also be used to achieve the sense, antisense or triplex inhibition of a target nucleic acid. For example, vectors containing antisense nucleic acids can be employed to express protein or antisense message to reduce the expression of the target nucleic acid and therefore its activity.

A specific example of DNA viral vector for introducing and expressing antisense nucleic acids is the adenovirus derived vector Adenop53TK. This vector expresses a herpes virus thymidine kinase (TK) gene for either positive or negative selection and an expression cassette for desired recombinant sequences such as antisense sequences. This vector can be used to infect cells that have an adenovirus receptor which includes most cancers of epithelial origin as well as others. This vector as well as others that exhibit similar desired functions can be used to treat a mixed population of cells include, for example, an in vitro or ex vivo culture of cells, a tissue or a human subject.

Additional features can be added to the vector to ensure its safety and/or enhance its therapeutic efficacy. Such features include, for example, markers that can be used to negatively select against cells infected with the recombinant virus. An example of such a negative selection marker is the TK gene described above that confers sensitivity to the anti-viral gancyclovir. Negative selection is therefore a means by which infection can be controlled because it provides inducible suicide through the addition of antibiotic. Such protection ensures that if, for example, mutations arise that produce altered forms of the viral vector or sequence, cellular transformation will not occur. Features that limit expression to particular cell types can also be included. Such features include, for example, promoter and regulatory elements that are specific for the desired cell type.

Recombinant viral vectors are another example of vectors useful for in vivo expression of a desired nucleic acid because they offer advantages such as lateral infection and targeting specificity. Lateral infection is inherent in the life cycle of, for example, retrovirus and is the process by which a single infected cell produces many progeny virions that bud off and infect neighboring cells. The result is that a large area becomes rapidly infected, most of which was not initially infected by the original viral particles. This is in contrast to vertical-type of infection in which the infectious agent spreads only through daughter progeny. Viral vectors can also be produced that are unable to spread laterally. This characteristic can be useful if the desired purpose is to introduce a specified gene into only a localized number of targeted cells.

As described above, viruses are very specialized infectious agents that have evolved, in many cases, to elude host defense mechanisms. Typically, viruses infect and propagate in specific cell types. The targeting specificity of viral vectors utilizes its natural specificity to specifically target predetermined cell types and thereby introduce a recombinant gene into the infected cell. The vector to be used in the methods of the invention will depend on desired cell type to be targeted. For example, if breast cancer is to be treated, then a vector specific for such epithelial cells should be used. Likewise, if diseases or pathological conditions of the hematopoietic system are to be treated, then a viral vector that is specific for blood cells and their precursors, preferably for the specific type of hematopoietic cell, should be used.

Retroviral vectors can be constructed to function either as infectious particles or to undergo only a single initial round of infection. In the former case, the genome of the virus is modified so that it maintains all the necessary genes, regulatory sequences and packaging signals to synthesize new viral proteins and RNA. Once these molecules are synthesized, the host cell packages the RNA into new viral particles which are capable of undergoing further rounds of infection. The vector's genome is also engineered to encode and express the desired recombinant gene. In the case of non-infectious viral vectors, the vector genome is usually mutated to destroy the viral packaging signal that is required to encapsulate the RNA into viral particles. Without such a signal any particles that are formed will not contain a genome and therefore cannot proceed through subsequent rounds of infection. The specific type of vector will depend upon the intended application. The actual vectors are also known and readily available within the art or can be constructed by one skilled in the art using well-known methodology.

If viral vectors are used, for example, the procedure can take advantage of their target specificity and consequently, do not have to be administered locally at the diseased site. However, local administration may provide a quicker and more effective treatment, administration can also be performed by, for example, intravenous or subcutaneous injection into the subject. Injection of the viral vectors into a spinal fluid can also be used as a mode of administration, especially in the case of neurodegenerative diseases. Following injection, the viral vectors will circulate until they recognize host cells with the appropriate target specificity for infection.

Transfection vehicles such as liposomes can also be used to introduce the non-viral vectors described above into recipient cells within the inoculated area. Such transfection vehicles are known by one skilled within the art.

The present invention includes the construction of transgenic and knockout organisms that are exhibit the phenotypic manifestations of A-T.

According to the present invention, there is provided a method for diagnosing and detecting carriers of the defective gene responsible for causing A-T. Carrier detection is especially important since A-T mutations underlie certain cases of cancer predisposition in the general population. Identifying the carriers either by their defective gene or by their missing or defective protein(s) encoded thereby, leads to earlier and more consistent diagnosis of A-T gene carriers. Thus, since carriers of the disease are more likely to be cancer-prone and/or sensitive to therapeutic applications of radiation, better surveillance and treatment protocols can be initiated for them. Conversely, exclusion of A-T heterozygotes from patients undergoing radiotherapy can allow for establishing routinely higher dose schedules for other cancer patients thereby improving the efficacy of their treatment.

The method of carrier detection is carried out by first obtaining a sample of either cells or bodily fluid from a subject. Convenient methods for obtaining a cellular sample can include collection of either mouth wash fluids or hair roots. A cell sample could be amniotic or placental cells or tissue in the case of a prenatal diagnosis. A crude DNA could be made from the cells (or alternatively proteins isolated) by techniques well known in the art. This isolated target DNA is then used for PCR analysis (or alternatively, Western blot analysis for proteins) with appropriate primers derived from the gene sequence by techniques well known in the art. The PCR product would then be tested for the presence of appropriate sequence variations in order to assess genotypic A-T status of the subject.

In order to use the method of the present invention for diagnostic applications, it is advantageous to include a mechanism for identifying the presence or absence of target polynucleotide sequence (or alternatively proteins). In many hybridization based diagnostic or experimental procedures, a label or tag is used to detect or visualize for the presence or absence of a particular polynucleotide sequence. Typically, oligomer probes are labelled with radioisotopes such as $^{32}P$ or $^{35}S$ (Sambrook, 1992) which can be detected by methods well known in the art such as autoradiography. Oligomer probes can also be labelled by non-radioactive methods such as chemiluminescent materials which can be detected by autoradiography (Sambrook, 1992). Also, enzyme-substrate based labelling and detection methods can be used. Labelling can be accomplished by mechanisms well known in the art such as end labelling (Sambrook, 1992), chemical labelling, or by hybridization with another labelled oligonucleotide. These methods of labelling and detection are provided merely as examples and are not meant to provide a complete and exhaustive list of all the methods known in the art.

The introduction of a label for detection purposes can be accomplished by attaching the label to the probe prior to hybridization.

An alternative method for practicing the method of the present invention includes the step of binding the target DNA to a solid support prior to the application of the probe. The solid support can be any material capable of binding the target DNA, such as beads or a membranous material such as nitrocellulose or nylon. After the target DNA is bound to the solid support, the probe oligomers is applied.

The present invention also provides a kit for diagnosis and detection of the defective A-T gene. The kit includes a molecular probe complimentary to genetic sequences of the defective gene which causes ataxia-telangiectasia (A-T) and suitable labels for detecting hybridization of the molecular probe and the defective gene thereby indicating the presence of the defective gene. The molecular probe has a DNA sequence complementary to mutant sequences. Alternatively, the kit can contain reagents and antibodies for detection of mutant proteins.

Throughout this application various publications and patents are referenced by citation or number. Full citations for the publications referenced are listed below. The disclosures of these publications in their entireties are hereby incorporated by reference into this application in order to more fully describe the state of the art to which this invention pertains.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the appended claims, the invention may be practiced otherwise than as specifically described.

REFERENCES

Aksentijevitch et al., "Familial mediterranean fever in Moroccan Jews: Demonstration of a founder effect by extended haplotype analysis" Am. J. Hum. Genet., 53:644–651 (1993).

Ambrose et al., "A physical map across chromosome 11q22-23 containing the major locus for ataxia-telangiectasia", Genomics, 21:612–619 (1994).

Attree et al., "The Lowe's oculocerebrorenal syndrome gene encodes protein highly homologous to inositol polyphosphate-5-phosphatase" Nature, 358:239–242 (1992).

Barker, "A more robust, rapid alkaline denaturation sequencing method", BioTechniques, Vol. 14, No. 2, pp. 168–169 (1993).

Berger et al., "Isolation of a candidate gene for Norrie disease by positional cloning" Nature Genet. 1:199–203, (1992)

Buckler et al., "Exon amplification: a strategy to isolate mammalian genes ased on RNA splicing" Proc. Natl. Acad. Sci. USA, 88:4005–4009 (1991).

Burke and Olson, "Preparation of Clone Libraries in Yeast Artificial-Chromosome Vectors" in Methods in Enzymology, Vol. 194, "Guide to Yeast Genetics and Molecular Biology", eds. C. Guthrie and G. Fink, Academic Press, Inc., Chap. 17, pp. 251–270 (1991).

Capecchi, "Altering the genome by homologous recombination" Science 244:1288–1292 (1989).

Chakravarti et al., "Nonuniform recombination within the human beta-globin gene cluster" Am. J. Hum. Genet., 36:1239–1258 (1984).

Chelly et al., "Isolation of a candidate gene for Menkes disease that encodes a potential heavy metal binding protein" Nature Genet. 3:14–19 (1993).

Church et al., "Isolation of genes from complex sources of mammalian genomic DNA using exon amplification" Nature Genet. 6:98–104 (1993).

Collins, F. S. "Positional cloning: let's not call it reverse anymore" Nature Genet., 1:3–6 (1992).

Davies et al., "Targeted alterations in yeast artificial chromosomes for inter-species gene transfer", Nucleic Acids Research, Vol. 20, No. 11, pp. 2693–2698 (1992).

Dickinson et al., "High frequency gene targeting using insertional vectors", Human Molecular Genetics, Vol. 2, No. 8, pp. 1299–1302 (1993).

Duyk et al., "Exon trapping: A genetic screen to identify candidate transcribed sequences in cloned mammalian genomic DNA" Proc. Natl. Acad. Sci. USA, 87:8995–8999 (1990).

Fodor et al, "Multiplexed biochemical assays with biological chips", Nature 364:555–556 (1993)

Foroud et al. "Localization of the AT locus to an 8 cM interval defined by STMY and S132" *Am. J. Hum. Genet.*, 49:1263–1279 (1991).

Frohman, M. A. "On beyond classic RACE (rapid amplification of cDNA ends)" *PCR Methods and Applications*, 4:S40–S58 (1994).

Frohman et al., "Rapid production of full-length cDNAs from rare transcripts: Amplification using a single gene-specific oligonucleotide primer" *Proc. Natl. Acad. Sci. USA*, 85:8998–9002 (1988).

Gatti et al., "Genetic haplotyping of ataxia-telangiectasia families localizes the major gene to an 850 kb region on chromosome 11q23.1" *Int. J. Radiat. Biol.* (1994).

Gatti et al. "Localization of an ataxia-telangiectasia gene to chromosome 11q22-23" *Nature*, 336:577–580 (1988).

Gilboa, et al., "Transfer and expression of cloned genes using retroviral vectors" *BioTechniques* 4(6):504–512 (1986).

Hastbacka et al., "Linkage disequilibrium mapping in isolated founder populations: diastrophic dysplasia in Finland" *Nature Genet.*, 2:204–211 (1992).

Hogervorst et al., "Rapid detection of BRCA1 mutations by the protein truncation test" *Nature Genetics* 10:208–212 (1995).

Huxley et al., "The human HPRT gene on a yeast artificial chromosome is functional when transferred to mouse cells by cell fusion", *Genomics*, 9:742–750 (1991).

Jakobovits et al., "Germ-line transmission and expression of a human-derived yeast artificial chromosome", *Nature*, Vol. 362, pp. 255–261 (1993).

James et al., *Nature Genet.* 8:70 (1994).

Jaspers et al., *Cytogenet. Cell Genet.*, 49:259 (1988).

Kawasaki ES. Amplification of RNA. In: PCR protocols: A Guide to Methods and Applications, Innis MA, Gelfand DH, Sninsky JJ, White TJ, eds. Academic Press, 1990, pp21–27.

Kerem et al., "Identification of the cystic fibrosis gene: genetic analysis" *Science*, 245:1073–1080 (1989).

Lamb et al., "Introduction and expression of the 400 kilobase precursor amyloid protein gene in transgenic mice", *Nature Genetics*, Vol. 5, pp. 22–29 (1993).

Lange et al., "Localization of an ataxia-telangiectasia gene to a 850 kb interval on chromosome 11q23.1 by linkage analysis of 176 families in an international consortium" *Am. J. Hum. Genet.* (1995).

Lehesjoki et al., "Localization of the EPM1 gene for progressive myoclonus epilepsy on chromosome 21: linkage disequilibrium allows high resolution mapping" *Hum. Mol. Genet.*, 2:1229–1234 (1993).

Lichter, et al., "High-resolution mapping of human chromosome 11 by in situ hybridization with cosmid clones" *Science* 247:64–69 (1990).

Litt and Luty. "A hypervariable microsatellite revealed by in vitro amplification of a dinucleotide repeat within the cardiac muscle actin gene" *Am. J. Hum. Genet.*, 44:397–401 (1989).

Llerena et al., "Spontaneous and induced chromosome breakage in chorionic villus samples: a cytogenetic approach to first trimester prenatal diagnosis of ataxia-telangiectasia syndrome" *J. Med. Genet.*, 26:174–178 (1989).

Lovett et al., *Proc. Natl. Acad. Sci. USA* 88, 9628 (1991)

McConville et al., "Genetic and physical mapping of the ataxia-telangiectasia locus on chromosome 11q22-23" *Int. J. Radiat. Biol.* (1994).

McConville et al., "Paired STSs amplified from radiation hybrids, and from associated YACs, identify highly polymorphic loci flanking the ataxia-telangiectasia locus on chromosome 11q22-23" *Hum. Mol. Genet.*, 2:969–974 (1993).

McConville et al., "Fine mapping of the chromosome 11q22-23 region using PFGE, linkage and haplotype analysis; localization of the gene for ataxia telangiectasia to a 5 cM region flanked by NCAM/DRD2 and STMY/CJ52.75, phi2.22" *Nucleic Acids Res.*, 18:4335–4343 (1990).

Miki et al. "A strong candidate for the breast and ovarian cancer susceptibility gene BRCA1" *Science*, 266:66–71 (1994).

Mitchison et al., "Fine genetic mapping of the Batten Disease locus (CLN3) by haplotype analysis and demonstration of allelic association with chromosome 16p microsatellite loci" *Genomics*, 16:455–460 (1993).

Morgan et al., "The selective isolation of novel cDNAs encoded by the regions surrounding the human interleukin 4 and 5 genes" *Nucleic Acids Res*, 20:5173–5179 (1992).

Orita M. et al. Detection of polymorphisms of human DNA by gel electrophoresis as single-strand conformation polymorphisms. Proc Natl Acad Sci USA 1989; 86:2766–2770

Oskato et al., "Ataxia-telangiectasia: allelic association with 11q22-23 markers in Moroccan-Jewish patients". 43rd Annual Meeting of the American Society of Human Genetics, New Orleans, La. (1993).

Ozelius et al., "Strong alleleic association between the torsion dystonia gene (DYT1) and loci on chromosome 9q34 in Ashkenazi Jews" *Am. J. Hum. Genet.* 50:619–628 (1992).

Parimoo et al., "cDNA selection: Efficient PCR approach for the selection of cDNAs encoded in large chromosomal DNA fragments" *Proc. Natl. Acad. Sci. USA*, 88:9623–9627 (1991).

Pease et al., "Light-generated oligonucleotide arrays for rapid DNA sequence analysis", *Proc. Natl. Acad. Sci. USA* 91(11):5022–5026 (1994)

Richard et al., *Genomics* 17, 1 (1993).

Rothstein, "Targeting, disruption, replacement, and allele rescue: integrative DNA transformation in yeast" in *Methods in Enzymology*, Vol. 194, "Guide to Yeast Genetics and Molecular Biology", eds. C. Guthrie and G. Fink, Academic Press, Inc., Chap. 19, pp. 281–301 (1991).

Rotman et al., "Three dinucleotide repeat polymorphisms at the ataxia-telangiectasia locus" *Human Molecular Genetics* (1994b).

Rotman et al., "A YAC contig spanning the ataxia-telangiectasia locus (groups A and C) on chromosome 11q22-23". *Genomics* (1994c).

Rotman et al., "Physical and genetic mapping of the ATA/ATC locus in chromosome 11q22-23" *Int. J. Radiat. Biol.* (1994d).

Rotman et al., "Rapid identification of polymorphic CA-repeats in YAC clones" *Molecular Biotechnology* (1995).

Savitsky et al., "A single gene with homologies to phosphatidylinositol 3-kinases and rad3+ is Mutated all complementation groups of ataxia-telangiectasia" *Science*, 268:1749–1753 (June 23, 1995)

Schedl et al., "A yeast artificial chromosome covering the tyrosinase gene confers copy number-dependent expression in transgenic mice", *Nature*, Vol. 362, pp. 258–261 (1993).

Sirugo et al., "Friedreich ataxia in Louisiana Acadians: Demonstration of a founder effect by analysis of microsatellite-generated extended haplotypes" *Am. J. Hum. Genet.*, 50:559–566 (1992).

We claim:

1. A purified ataxia-telangiectasia protein encoded by the nucleic acid sequence consisting of SEQ ID No:1 or SEQ ID No:3.

2. A purified protein having an amino acid sequence selected from the group consisting of SEQ ID No:2 and mutations of SEQ ID No:2 which cause ataxia-telangiectasia.

3. A peptide having the amino acid sequence selected from the group consisting of
HEPANSSASQSTDLC (SEQ ID No:4),
CKRNLSDIDQSFDKV (SEQ ID No:5),
PEDETELHPTLNADDQEC (SEQ ID No:6), and
CKSLASFIKKPFDRGEVESMEDDTNG (SEQ ID No:7).

4. The protein of claim 2 wherein said protein is truncated as a result of a mutation event.

5. The protein of claim 2 wherein the mutations are as set forth in Table 1 which contains a listing of mutations which cause protein truncation and thereby ataxia-telangiectasia.

* * * * *

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:
 ( A ) LENGTH: 7410 base pairs
 ( B ) TYPE: nucleic acid
 ( C ) STRANDEDNESS: single
 ( D ) TOPOLOGY: linear ( x i ) SEQUENCE DESCRIPTION: SEQ ID NO:1:

| | | | | | | |
|---|---|---|---|---|---|---|
| CGACAAATGA | GGAATTCAGA | ATTGGTTCCT | TGAGAAATAT | GATGCAGCTA | TGTACACGTT | 60 |
| GCTTGAGCAA | CTGTACCAAG | AAGAGTCCAA | ATAAGATTGC | ATCTGGCTTT | TTCCTGCGAT | 120 |
| TGTTAACATC | AAAGCTAATG | AATGACATTG | CAGATATTTG | TAAAAGTTTA | GCATCCTTCA | 180 |
| TCAAAAAGCC | ATTTGACCGT | GGAGAAGTAG | AATCAATGGA | AGATGATACT | AATGGAAATC | 240 |
| TAATGGAGGT | GGAGGATCAG | TCATCCATGA | ATCTATTTAA | CGATTACCCT | GATAGTAGTG | 300 |
| TTAGTGATGC | AAACGAACCT | GGAGAGAGCC | AAAGTACCAT | AGGTGCCATT | AATCCTTTAG | 360 |
| CTGAAGAATA | TCTGTCAAAG | CAAGATCTAC | TTTTCTTAGA | CATGCTCAAG | TTCTTGTGTT | 420 |
| TGTGTGTAAC | TACTGCTCAG | ACCAATACTG | TGTCCTTTAG | GGCAGCTGAT | ATTCGGAGGA | 480 |
| AATTGTTAAT | GTTAATTGAT | TCTAGCACGC | TAGAACCTAC | CAAATCCCTC | CACCTGCATA | 540 |
| TGTATCTAAT | GCTTTTAAAG | GAGCTTCCTG | GAGAAGAGTA | CCCCTTGCCA | ATGGAAGATG | 600 |
| TTCTTGAACT | TCTGAAACCA | CTATCCAATG | TGTGTTCTTT | GTATCGTCGT | GACCAAGATG | 660 |
| TTTGTAAAAC | TATTTTAAAC | CATGTCCTTC | ATGTAGTGAA | AAACCTAGGT | CAAAGCAATA | 720 |
| TGGACTCTGA | GAACACAAGG | GATGCTCAAG | GACAGTTTCT | TACAGTAATT | GGAGCATTTT | 780 |
| GGCATCTAAC | AAAGGAGAGG | AAATATATAT | TCTCTGTAAG | AATGGCCCTA | GTAAATTGCC | 840 |
| TTAAAACTTT | GCTTGAGGCT | GATCCTTATT | CAAAATGGGC | CATTCTTAAT | GTAATGGGAA | 900 |
| AAGACTTTCC | TGTAAATGAA | GTATTTACAC | AATTTCTTGC | TGACAATCAT | CACCAAGTTC | 960 |
| GCATGTTGGC | TGCAGAGTCA | ATCAATAGAT | TGTTCCAGGA | CACGAAGGGA | GATTCTTCCA | 1020 |
| GGTTACTGAA | AGCACTTCCT | TTGAAGCTTC | AGCAAACAGC | TTTTGAAAAT | GCATACTTGA | 1080 |
| AAGCTCAGGA | AGGAATGAGA | GAAATGTCCC | ATAGTGCTGA | GAACCCTGAA | ACTTTGGATG | 1140 |
| AAATTTATAA | TAGAAAATCT | GTTTTACTGA | CGTTGATAGC | TGTGGTTTTA | TCCTGTAGCC | 1200 |
| CTATCTGCGA | AAAACAGGCT | TTGTTTGCCC | TGTGTAAATC | TGTGAAAGAG | AATGGATTAG | 1260 |
| AACCTCACCT | TGTGAAAAAG | GTTTAGAGA | AAGTTTCTGA | AACTTTTGGA | TATAGACGTT | 1320 |
| TAGAAGACTT | TATGGCATCT | CATTTAGATT | ATCTGGTTTT | GGAATGGCTA | AATCTTCAAG | 1380 |
| ATACTGAATA | CAACTTATCT | TCTTTTCCTT | TTATTTTATT | AAACTACACA | AATATTGAGG | 1440 |
| ATTTCTATAG | ATCTTGTTAT | AAGGTTTTGA | TTCCACATCT | GGTGATTAGA | AGTCATTTTG | 1500 |
| ATGAGGTGAA | GTCCATTGCT | AATCAGATTC | AAGAGGACTG | GAAAAGTCTT | CTAACAGACT | 1560 |
| GCTTTCCAAA | GATTCTTGTA | AATATTCTTC | CTTATTTTGC | CTATGAGGGT | ACCAGAGACA | 1620 |
| GTGGGATGGC | ACAGCAAAGA | GAGACTGCTA | CCAAGGTCTA | TGATATGCTT | AAAAGTGAAA | 1680 |
| ACTTATTGGG | AAAACAGATT | GATCACTTAT | TCATTAGTAA | TTTACCAGAG | ATTGTGGTGG | 1740 |
| AGTTATTGAT | GACGTTACAT | GAGCCAGCAA | ATTCTAGTGC | CAGTCAGAGC | ACTGACCTCT | 1800 |

-continued

```
GTGACTTTTC AGGGGATTTG GATCCTGCTC CTAATCCACC TCATTTTCCA TCGCATGTGA    1860
TTAAAGCAAC ATTTGCCTAT ATCAGCAATT GTCATAAAAC CAAGTAAAAA AGCATTTTAG    1920
AAATTCTTTC CAAAAGCCCT GATTCCTATC AGAAAATTCT TCTTGCCATA TGTGAGCAAG    1980
CAGCTGAAAC AAATAATGTT TATAAGAAGC ACAGAATTCT TAAAATATAT CACCTGTTTG    2040
TTAGTTTATT ACTGAAAGAT ATAAAAGTG GCTTAGGAGG AGCTTGGGCC TTTGTTCTTC     2100
GAGACGTTAT TTATACTTTG ATTCACTATA TCAACCAAAG GCCTTCTTGT ATCATGGATG    2160
TGTCATTACG TAGCTTCTCC CTTTGTTGTG ACTTATTAAG TCAGGTTTGC CAGACAGCCG    2220
TGACTTACTG TAAGGATGCT CTAGAAAACC ATCTTCATGT TATTGTTGGT ACACTTATAC    2280
CCCTTGTGTA TGAGCAGGTG GAGGTTCAGA AACAGGTATT GGACTTGTTG AAATACTTAG    2340
TGATAGATAA CAAGGATAAT GAAAACCTCT ATATCACGAT TAAGCTTTTA GATCCTTTTC    2400
CTGACCATGT TGTTTTTAAG GATTTGCGTA TTACTCAGCA AAAAATCAAA TACAGTAGAG    2460
GACCCTTTTC ACTCTTGGAG GAAATTAACC ATTTTCTCTC AGTAAGTGTT TATGATGCAC    2520
TTCCATTGAC AAGACTTGAA GGACTAAAGG ATCTTCGAAG ACAACTGGAA CTACATAAAG    2580
ATCAGATGGT GGACATTATG AGAGCTTCTC AGGATAATCC GCAAGATGGG ATTATGGTGA    2640
AACTAGTTGT CAATTTGTTG CAGTTATCCA AGATGGCAAT AAACCACACT GGTGAAAAAG    2700
AAGTTCTAGA GGCTGTTGGA AGCTGCTTGG GAGAAGTGGG TCCTATAGAT TTCTCTACCA    2760
TAGCTATACA ACATAGTAAA GATGCATCTT ATACCAAGGC CCTTAAGTTA TTTGAAGATA    2820
AAGAACTTCA GTGGACCTTC ATAATGCTGA CCTACCTGAA TAACACACTG GTAGAAGATT    2880
GTGTCAAAGT TCGATCAGCA GCTGTTACCT GTTTGAAAAA CATTTTAGCC ACAAAGACTG    2940
GACATAGTTT CTGGGAGATT TATAAGATGA CAACAGATCC AATGCTGGCC TATCTACAGC    3000
CTTTTAGAAC ATCAAGAAAA AAGTTTTTAG AAGTACCCAG ATTTGACAAA GAAAACCCTT    3060
TTGAAGGCCT GGATGATATA AATCTGTGGA TTCCTCTAAG TGAAAATCAT GACATTTGGA    3120
TAAAGACACT GACTTGTGCT TTTTTGGACA GTGGAGGCAC AAAAATGTGAA ATTCTTCAAT   3180
TATTAAAGCC AATGTGTGAA GTGAAAACTG ACTTTGTCA GACTGTACTT CCATACTTGA    3240
TTCATGATAT TTTACTCCAA GATACAAATG AATCATGGAG AAATCTGCTT TCTACACATG    3300
TTCAGGGATT TTTCACCAGC TGTCTTCGAC ACTTCTCGCA ACGAGCCGA TCCACAACCC     3360
CTGCAAACTT GGATTCAGAG TCAGAGCACT TTTTCCGATG CTGTTTGGAT AAAAAATCAC    3420
AAAGAACAAT GCTTGCTGTT GTGGACTACA TGAAGACA AAAGAGACCT TCTTCAGGAA      3480
CAATTTTTAA TGATGCTTTC TGGCTGGATT TAAATTATCT AGAAGTTGCC AAGGTAGCTC    3540
AGTCTTGTGC TGCTCACTTT ACAGCTTTAC TCTATGCAGA AATCTATGCA GATAAGAAAA    3600
GTATGGATGA TCAAGAGAAA AGAAGTCTTG CATTGAAGA AGGAAGCCAG AGTACAACTA     3660
TTTCTAGCTT GAGTGAAAAA AGTAAAGAAG AAACTGGAAT AAGTTTACAG GATCTTCTCT    3720
TAGAAATCTA CAGAAGTATA GGGGAGCCAG ATAGTTTGTA TGGCTGTGGT GGAGGGAAGA    3780
TGTTACAACC CATTACTAGA CTACGAACAT ATGAACACGA AGCAATGTGG GGCAAAGCCC    3840
TAGTAACATA TGACCTCGAA ACAGCAATCC CCTCATCAAC ACGCCAGGCA GGAATCATTC    3900
AGGCCTTGCA GAATTTGGGA CTCTGCCATA TTCTTTCCGT CTATTTAAAA GGATTGGATT    3960
ATGAAAATAA AGACTGGTGT CCTGAACTAG AAGAACTTCA TTACCAAGCA GCATGGAGGA    4020
ATATGCAGTG GGACCATTGC ACTTCCGTCA GCAAAGAAGT AGAAGGAACC AGTTACCATG    4080
AATCATTGTA CAATGCTCTA CAATCTCTAA GAGACAGAGA ATTCTCTACA TTTTATGAAA    4140
GTCTCAAATA TGCCAGAGTA AAAGAAGTGG AAGAGATGTG TAAGCGCAGC CTTGAGTCTG    4200
```

```
TGTATTCGCT CTATCCCACA CTTAGCAGGT TGCAGGCCAT TGGAGAGCTG GAAAGCATTG    4260
GGGAGCTTTT CTCAAGATCA GTCACACATA GACAACTCTC TGAAGTATAT ATTAAGTGGC    4320
AGAAACACTC CCAGCTTCTC AAGGACAGTG ATTTTAGTTT TCAGGAGCCT ATCATGGCTC    4380
TACGCACAGT CATTTTGGAG ATCCTGATGG AAAAGGAAAT GGACAACTCA CAAAGAGAAT    4440
GTATTAAGGA CATTCTCACC AAACACCTTG TAGAACTCTC TATACTGGCC AGAACTTTCA    4500
AGAACACTCA GCTCCCTGAA AGGGCAATAT TTCAAATTAA ACAGTACAAT TCAGTTAGCT    4560
GTGGAGTCTC TGAGTGGCAG CTGGAAGAAG CACAAGTATT CTGGGCAAAA AAGGAGCAGA    4620
GTCTTGCCCT GAGTATTCTC AAGCAAATGA TCAAGAAGTT GGATGCCAGC TGTGCAGCGA    4680
ACAATCCCAG CCTAAAACTT ACATACACAG AATGTCTGAG GGTTTGTGGC AACTGGTTAG    4740
CAGAAACGTG CTTAGAAAAT CCTGCGGTCA TCATGCAGAC CTATCTAGAA AAGGCAGTAG    4800
AAGTTGCTGG AAATTATGAT GGAGAAAGTA GTGATGAGCT AAGAAATGGA AAAATGAAGG    4860
CATTTCTCTC ATTAGCCCGG TTTTCAGATA CTCAATACCA AGAATTGAA AACTACATGA    4920
AATCATCGGA ATTTGAAAAC AAGCAAGCTC TCCTGAAAAG AGCCAAGAG GAAGTAGGTC    4980
TCCTTAGGGA ACATAAAATT CAGACAAACA GATACACAGT AAAGGTTCAG CGAGAGCTGG    5040
AGTTGGATGA ATTAGCCCTG CGTGCACTGA AAGAGGATCG TAAACGCTTC TTATGTAAAG    5100
CAGTTGAAAA TTATATCAAC TGCTTATTAA GTGGAGAAGA ACATGATATG TGGGTATTCC    5160
GGCTTTGTTC CCTCTGGCTT GAAAATTCTG GAGTTTCTGA AGTCAATGGC ATGATGAAGA    5220
GAGACGGAAT GAAGATTCCA ACATATAAAT TTTGCCTCT TATGTACCAA TTGGCTGCTA    5280
GAATGGGGAC CAAGATGATG GGAGGCCTAG GATTTCATGA AGTCCTCAAT AATCTAATCT    5340
CTAGAATTTC AATGGATCAC CCCCATCACA CTTTGTTTAT TATACTGGCC TTAGCAAATG    5400
CAAACAGAGA TGAATTTCTG ACTAAACCAG AGGTAGCCAG AAGAAGCAGA ATAACTAAAA    5460
ATGTGCCTAA ACAAAGCTCT CAGCTTGATG AGGATCGAAC AGAGGCTGCA AATAGAATAA    5520
TATGTACTAT CAGAAGTAGG AGACCTCAGA TGGTCAGAAG TGTTGAGGCA CTTTGTGATG    5580
CTTATATTAT ATTAGCAAAC TTAGATGCCA CTCAGTGGAA GACTCAGAGA AAAGGCATAA    5640
ATATTCCAGC AGACCAGCCA ATTACTAAAC TTAAGAATTT AGAAGATGTT GTTGTCCCTA    5700
CTATGGAAAT TAAGGTGGAC CACACAGGAG AATATGGAAA TCTGGTGACT ATACAGTCAT    5760
TTAAAGCAGA ATTTCGCTTA GCAGGAGGTG TAAATTTACC AAAAATAATA GATTGTGTAG    5820
GTTCCGATGG CAAGGAGAGG AGACAGCTTG TTAAGGGCCG TGATGACCTG AGACAAGATG    5880
CTGTCATGCA ACAGGTCTTC CAGATGTGTA ATACATTACT GCAGAGAAAC ACGGAAACTA    5940
GGAAGAGGAA ATTAACTATC TGTACTTATA AGGTGGTTCC CCTCTCTCAG CGAAGTGGTG    6000
TTCTTGAATG GTGCACAGGA ACTGTCCCCA TTGGTGAATT TCTTGTTAAC AATGAAGATG    6060
GTGCTCATAA AAGATACAGG CCAAATGATT TCAGTGCCTT TCAGTGCCAA AAGAAAATGA    6120
TGGAGGTGCA AAAAAAGTCT TTTGAAGAGA AATATGAAGT CTTCATGGAT GTTTGCCAAA    6180
ATTTTCAACC AGTTTTCCGT TACTTCTGCA TGGAAAAATT CTTGGATCCA GCTATTTGGT    6240
TTGAGAAGCG ATTGGCTTAT ACGCGCAGTG TAGCTACTTC TTCTATTGTT GGTTACATAC    6300
TTGGACTTGG TGATAGACAT GTACAGAATA TCTTGATAAA TGAGCAGTCA GCAGAACTTG    6360
TACATATAGA TCTAGGTGTT GCTTTTGAAC AGGGCAAAAT CCTTCCTACT CCTGAGACAG    6420
TTCCTTTTAG ACTCACCAGA GATATTGTGG ATGGCATGGG CATTACGGGT GTTGAAGGTG    6480
TCTTCAGAAG ATGCTGTGAG AAAACCATGG AAGTGATGAG AAACTCTCAG GAAACTCTGT    6540
TAACCATTGT AGAGGTCCTT CTATATGATC CACTCTTTGA CTGGACCATG AATCCTTTGA    6600
```

```
AAGCTTTGTA TTTACAGCAG AGGCCGGAAG ATGAAACTGA GCTTCACCCT ACTCTGAATG    6660
CAGATGACCA AGAATGCAAA CGAAATCTCA GTGATATTGA CCAGAGTTTC GACAAAGTAG    6720
CTGAACGTGT CTTAATGAGA CTACAAGAGA AACTGAAAGG AGTGGAAGAA GGCACTGTGC    6780
TCAGTGTTGG TGGACAGGTG AATTTGCTCA TACAGCAGGC CATAGACCCC AAAAATCTCA    6840
GCCGACTTTT CCCAGGATGG AAAGCTTGGG TGTGATCTTC AGTATATGAA TTACCCTTTC    6900
ATTCAGCCTT TAGAAATTAT ATTTTAGCCT TTATTTTTAA CCTGCCAACA TACTTTAAGT    6960
AGGGATTAAT ATTTAAGTGA ACTATTGTGG GTTTTTTTGA ATGTTGGTTT TAATACTTGA    7020
TTTAATCACC ACTCAAAAAT GTTTTGATGG TCTTAAGGAA CATCTCTGCT TTCACTCTTT    7080
AGAAATAATG GTCATTCGGG CTGGGCGCAG CGGCTCACGC CTGTAATCCC AGCACTTTGG    7140
GAGGCCGAGG TGAGCGGATC ACAAGGTCAG GAGTTCGAGA CCAGCCTGGC CAAGAGACCA    7200
GCCTGGCCAG TATGGTGAAA CCCTGTCTCT ACTAAAAATA CAAAAATTAG CCGAGCATGG    7260
TGGCGGGCAC CTGTAGTCCC AGCTACTCGA GAGGCTGAGG CAGGAGAATC TCTTGAACCT    7320
GGGAGGTGAA GGTTGCTGTG GGCCAAAATC ATGCCATTGC ACTCCAGCCT GGGTGACAAG    7380
AGCGAAACTC CATCTCAAAA AWWAAAAAAA                                    7410
```

( 2 ) INFORMATION FOR SEQ ID NO:2:

( i ) SEQUENCE CHARACTERISTICS:
        ( A ) LENGTH: 1708 amino acids
        ( B ) TYPE: amino acid
        ( C ) STRANDEDNESS: single
        ( D ) TOPOLOGY: linear ( x i ) SEQUENCE DESCRIPTION: SEQ ID NO:2:

```
Met Thr Leu His Glu Pro Ala Asn Ser Ser Ala Ser Gln Ser Thr Asp
 1               5                  10                  15

Leu Cys Asp Phe Ser Gly Asp Leu Asp Pro Ala Pro Asn Pro Pro His
            20                  25                  30

Phe Pro Ser His Val Ile Lys Ala Thr Phe Ala Tyr Ile Ser Asn Cys
        35                  40                  45

His Lys Thr Lys Leu Lys Ser Ile Leu Glu Ile Leu Ser Lys Ser Pro
    50                  55                  60

Asp Ser Tyr Gln Lys Ile Leu Leu Ala Ile Cys Glu Gln Ala Ala Glu
65                  70                  75                  80

Thr Asn Asn Val Tyr Lys Lys His Arg Ile Leu Lys Ile Tyr His Leu
                85                  90                  95

Phe Val Ser Leu Leu Leu Lys Asp Ile Lys Ser Gly Leu Gly Gly Ala
            100                 105                 110

Trp Ala Phe Val Leu Arg Asp Val Ile Tyr Thr Leu Ile His Tyr Ile
        115                 120                 125

Asn Gln Arg Pro Ser Cys Ile Met Asp Val Ser Leu Arg Ser Phe Ser
    130                 135                 140

Leu Cys Cys Asp Leu Leu Ser Gln Val Cys Gln Thr Ala Val Thr Tyr
145                 150                 155                 160

Cys Lys Asp Ala Leu Glu Asn His Leu His Val Ile Val Gly Thr Leu
                165                 170                 175

Ile Pro Leu Val Tyr Glu Gln Val Glu Val Gln Lys Gln Val Leu Asp
            180                 185                 190

Leu Leu Lys Tyr Leu Val Ile Asp Asn Lys Asp Asn Glu Asn Leu Tyr
        195                 200                 205

Ile Thr Ile Lys Leu Leu Asp Pro Phe Pro Asp His Val Val Phe Lys
```

|     |     |     | 210 |     |     |     | 215 |     |     |     | 220 |     |     |     |
|-----|-----|-----|-----|-----|-----|-----|-----|-----|-----|-----|-----|-----|-----|-----|
| Asp | Leu | Arg | Ile | Thr | Gln | Gln | Lys | Ile | Lys | Tyr | Ser | Arg | Gly | Pro | Phe |
| 225 |     |     |     |     | 230 |     |     |     |     | 235 |     |     |     | 240 |
| Ser | Leu | Leu | Glu | Glu | Ile | Asn | His | Phe | Leu | Ser | Val | Ser | Val | Tyr | Asp |
|     |     |     |     | 245 |     |     |     |     | 250 |     |     |     |     | 255 |
| Ala | Leu | Pro | Leu | Thr | Arg | Leu | Glu | Gly | Leu | Lys | Asp | Leu | Arg | Arg | Gln |
|     |     |     |     | 260 |     |     |     |     | 265 |     |     |     |     | 270 |
| Leu | Glu | Leu | His | Lys | Asp | Gln | Met | Val | Asp | Ile | Met | Arg | Ala | Ser | Gln |
|     |     |     | 275 |     |     |     |     | 280 |     |     |     |     | 285 |
| Asp | Asn | Pro | Gln | Asp | Gly | Ile | Met | Val | Lys | Leu | Val | Val | Asn | Leu | Leu |
|     | 290 |     |     |     |     | 295 |     |     |     |     | 300 |
| Gln | Leu | Ser | Lys | Met | Ala | Ile | Asn | His | Thr | Gly | Glu | Lys | Glu | Val | Leu |
| 305 |     |     |     |     | 310 |     |     |     |     | 315 |     |     |     |     | 320 |
| Glu | Ala | Val | Gly | Ser | Cys | Leu | Gly | Glu | Val | Gly | Pro | Ile | Asp | Phe | Ser |
|     |     |     |     | 325 |     |     |     |     | 330 |     |     |     |     | 335 |
| Thr | Ile | Ala | Ile | Gln | His | Ser | Lys | Asp | Ala | Ser | Tyr | Thr | Lys | Ala | Leu |
|     |     |     | 340 |     |     |     |     | 345 |     |     |     |     | 350 |
| Lys | Leu | Phe | Glu | Asp | Lys | Glu | Leu | Gln | Trp | Thr | Phe | Ile | Met | Leu | Thr |
|     |     | 355 |     |     |     |     | 360 |     |     |     |     | 365 |
| Tyr | Leu | Asn | Asn | Thr | Leu | Val | Glu | Asp | Cys | Val | Lys | Val | Arg | Ser | Ala |
|     | 370 |     |     |     |     | 375 |     |     |     |     | 380 |
| Ala | Val | Thr | Cys | Leu | Lys | Asn | Ile | Leu | Ala | Thr | Lys | Thr | Gly | His | Ser |
| 385 |     |     |     |     | 390 |     |     |     |     | 395 |     |     |     |     | 400 |
| Phe | Trp | Glu | Ile | Tyr | Lys | Met | Thr | Thr | Asp | Pro | Met | Leu | Ala | Tyr | Leu |
|     |     |     |     | 405 |     |     |     |     | 410 |     |     |     |     | 415 |
| Gln | Pro | Phe | Arg | Thr | Ser | Arg | Lys | Lys | Phe | Leu | Glu | Val | Pro | Arg | Phe |
|     |     |     | 420 |     |     |     |     | 425 |     |     |     |     | 430 |
| Asp | Lys | Glu | Asn | Pro | Phe | Glu | Gly | Leu | Asp | Asp | Ile | Asn | Leu | Trp | Ile |
|     |     |     | 435 |     |     |     |     | 440 |     |     |     |     | 445 |
| Pro | Leu | Ser | Glu | Asn | His | Asp | Ile | Trp | Ile | Lys | Thr | Leu | Thr | Cys | Ala |
|     | 450 |     |     |     |     | 455 |     |     |     |     | 460 |
| Phe | Leu | Asp | Ser | Gly | Gly | Thr | Lys | Cys | Glu | Ile | Leu | Gln | Leu | Leu | Lys |
| 465 |     |     |     |     | 470 |     |     |     |     | 475 |     |     |     |     | 480 |
| Pro | Met | Cys | Glu | Val | Lys | Thr | Asp | Phe | Cys | Gln | Thr | Val | Leu | Pro | Tyr |
|     |     |     |     | 485 |     |     |     |     | 490 |     |     |     |     | 495 |
| Leu | Ile | His | Asp | Ile | Leu | Leu | Gln | Asp | Thr | Asn | Glu | Ser | Trp | Arg | Asn |
|     |     |     | 500 |     |     |     |     | 505 |     |     |     |     | 510 |
| Leu | Leu | Ser | Thr | His | Val | Gln | Gly | Phe | Phe | Thr | Ser | Cys | Leu | Arg | His |
|     |     | 515 |     |     |     |     | 520 |     |     |     |     | 525 |
| Phe | Ser | Gln | Thr | Ser | Arg | Ser | Thr | Thr | Pro | Ala | Asn | Leu | Asp | Ser | Glu |
|     | 530 |     |     |     |     | 535 |     |     |     |     | 540 |
| Ser | Glu | His | Phe | Phe | Arg | Cys | Cys | Leu | Asp | Lys | Lys | Ser | Gln | Arg | Thr |
| 545 |     |     |     |     | 550 |     |     |     |     | 555 |     |     |     |     | 560 |
| Met | Leu | Ala | Val | Val | Asp | Tyr | Met | Arg | Arg | Gln | Lys | Arg | Pro | Ser | Ser |
|     |     |     |     | 565 |     |     |     |     | 570 |     |     |     |     | 575 |
| Gly | Thr | Ile | Phe | Asn | Asp | Ala | Phe | Trp | Leu | Asp | Leu | Asn | Tyr | Leu | Glu |
|     |     |     | 580 |     |     |     |     | 585 |     |     |     |     | 590 |
| Val | Ala | Lys | Val | Ala | Gln | Ser | Cys | Ala | Ala | His | Phe | Thr | Ala | Leu | Leu |
|     |     | 595 |     |     |     |     | 600 |     |     |     |     | 605 |
| Tyr | Ala | Glu | Ile | Tyr | Ala | Asp | Lys | Lys | Ser | Met | Asp | Asp | Gln | Glu | Lys |
|     | 610 |     |     |     |     | 615 |     |     |     |     | 620 |
| Arg | Ser | Leu | Ala | Phe | Glu | Glu | Gly | Ser | Gln | Ser | Thr | Thr | Ile | Ser | Ser |
| 625 |     |     |     |     | 630 |     |     |     |     | 635 |     |     |     |     | 640 |

| | | | | | | | | | | | | | | |
|---|---|---|---|---|---|---|---|---|---|---|---|---|---|---|
| Leu | Ser | Glu | Lys | Ser<br>645 | Lys | Glu | Thr | Gly<br>650 | Ile | Ser | Leu | Gln | Asp<br>655 | Leu |
| Leu | Leu | Glu | Ile<br>660 | Tyr | Arg | Ser | Ile | Gly<br>665 | Glu | Pro | Asp | Ser<br>670 | Leu | Tyr | Gly |
| Cys | Gly | Gly<br>675 | Gly | Lys | Met | Leu | Gln<br>680 | Pro | Ile | Thr | Arg | Leu<br>685 | Arg | Thr | Tyr |
| Glu | His<br>690 | Glu | Ala | Met | Trp | Gly<br>695 | Lys | Ala | Leu | Val | Thr<br>700 | Tyr | Asp | Leu | Glu |
| Thr<br>705 | Ala | Ile | Pro | Ser | Ser<br>710 | Thr | Arg | Gln | Ala | Gly<br>715 | Ile | Ile | Gln | Ala | Leu<br>720 |
| Gln | Asn | Leu | Gly | Leu<br>725 | Cys | His | Ile | Leu | Ser<br>730 | Val | Tyr | Leu | Lys | Gly<br>735 | Leu |
| Asp | Tyr | Glu | Asn<br>740 | Lys | Asp | Trp | Cys | Pro<br>745 | Glu | Leu | Glu | Glu<br>750 | Leu | His | Tyr |
| Gln | Ala | Ala<br>755 | Trp | Arg | Asn | Met | Gln<br>760 | Trp | Asp | His | Cys | Thr<br>765 | Ser | Val | Ser |
| Lys | Glu<br>770 | Val | Glu | Gly | Thr | Ser<br>775 | Tyr | His | Glu | Ser | Leu<br>780 | Tyr | Asn | Ala | Leu |
| Gln | Ser | Leu | Arg | Asp | Arg<br>790 | Glu | Phe | Ser | Thr | Phe<br>795 | Tyr | Glu | Ser | Leu | Lys<br>800 |
| Tyr | Ala | Arg | Val | Lys<br>805 | Glu | Val | Glu | Glu | Met<br>810 | Cys | Lys | Arg | Ser | Leu<br>815 | Glu |
| Ser | Val | Tyr | Ser<br>820 | Leu | Tyr | Pro | Thr | Leu<br>825 | Ser | Arg | Leu | Gln<br>830 | Ala | Ile | Gly |
| Glu | Leu | Glu | Ser<br>835 | Ile | Gly | Glu | Leu<br>840 | Phe | Ser | Arg | Ser | Val<br>845 | Thr | His | Arg |
| Gln | Leu | Ser<br>850 | Glu | Val | Tyr | Ile | Lys<br>855 | Trp | Gln | Lys | His | Ser<br>860 | Gln | Leu | Leu |
| Lys<br>865 | Asp | Ser | Asp | Phe | Ser<br>870 | Phe | Gln | Glu | Pro | Ile<br>875 | Met | Ala | Leu | Arg | Thr<br>880 |
| Val | Ile | Leu | Glu | Ile<br>885 | Leu | Met | Glu | Lys | Glu<br>890 | Met | Asp | Asn | Ser | Gln<br>895 | Arg |
| Glu | Cys | Ile | Lys<br>900 | Asp | Ile | Leu | Thr | Lys<br>905 | His | Leu | Val | Glu | Leu<br>910 | Ser | Ile |
| Leu | Ala | Arg<br>915 | Thr | Phe | Lys | Asn | Thr<br>920 | Gln | Leu | Pro | Glu | Arg<br>925 | Ala | Ile | Phe |
| Gln | Ile<br>930 | Lys | Gln | Tyr | Asn | Ser<br>935 | Val | Ser | Cys | Gly | Val<br>940 | Ser | Glu | Trp | Gln |
| Leu<br>945 | Glu | Glu | Ala | Gln | Val<br>950 | Phe | Trp | Ala | Lys | Lys<br>955 | Glu | Gln | Ser | Leu | Ala<br>960 |
| Ser | Leu | Ile | Leu | Lys<br>965 | Gln | Met | Ile | Lys | Lys<br>970 | Leu | Asp | Ala | Ser | Cys<br>975 | Ala |
| Ala | Asn | Asn | Pro<br>980 | Ser | Leu | Lys | Leu | Thr<br>985 | Tyr | Thr | Glu | Cys | Leu<br>990 | Arg | Val |
| Cys | Gly | Asn<br>995 | Trp | Leu | Ala | Glu | Thr<br>1000 | Cys | Leu | Glu | Asn | Pro<br>1005 | Ala | Val | Ile |
| Met | Gln | Thr<br>1010 | Tyr | Leu | Glu | Lys | Ala<br>1015 | Val | Glu | Val | Ala | Gly<br>1020 | Asn | Tyr | Asp |
| Gly<br>1025 | Glu | Ser | Ser | Asp | Glu<br>1030 | Leu | Arg | Asn | Gly | Lys<br>1035 | Met | Lys | Ala | Phe | Leu<br>1040 |
| Ser | Leu | Ala | Arg | Phe<br>1045 | Ser | Asp | Thr | Gln | Tyr<br>1050 | Gln | Arg | Ile | Glu | Asn<br>1055 | Tyr |
| Met | Lys | Ser | Ser<br>1060 | Glu | Phe | Glu | Asn | Lys<br>1065 | Gln | Ala | Leu | Leu | Lys<br>1070 | Arg | Ala |

```
Lys Glu Glu Val Gly Leu Leu Arg Glu His Lys Ile Gln Thr Asn Arg
    1075                1080                1085
Tyr Thr Val Lys Val Gln Arg Glu Leu Glu Leu Asp Glu Leu Ala Leu
    1090                1095                1100
Arg Ala Leu Lys Glu Asp Arg Lys Arg Phe Leu Cys Lys Ala Val Glu
1105                1110                1115                1120
Asn Tyr Ile Asn Cys Leu Leu Ser Gly Glu Glu His Asp Met Trp Val
                1125                1130                1135
Phe Arg Leu Cys Ser Leu Trp Leu Glu Asn Ser Gly Val Ser Glu Val
                1140                1145                1150
Asn Gly Met Met Lys Arg Asp Gly Met Lys Ile Pro Thr Tyr Lys Phe
    1155                1160                1165
Leu Pro Leu Met Tyr Gln Leu Ala Ala Arg Met Gly Thr Lys Met Met
    1170                1175                1180
Gly Gly Leu Gly Phe His Glu Val Leu Asn Asn Leu Ile Ser Arg Ile
1185                1190                1195                1200
Ser Met Asp His Pro His His Thr Leu Phe Ile Ile Leu Ala Leu Ala
                1205                1210                1215
Asn Ala Asn Arg Asp Glu Phe Leu Thr Lys Pro Glu Val Ala Arg Arg
                1220                1225                1230
Ser Arg Ile Thr Lys Asn Val Pro Lys Gln Ser Ser Gln Leu Asp Glu
    1235                1240                1245
Asp Arg Thr Glu Ala Ala Asn Arg Ile Ile Cys Thr Ile Arg Ser Arg
    1250                1255                1260
Arg Pro Gln Met Val Arg Ser Val Glu Ala Leu Cys Asp Ala Tyr Ile
1265                1270                1275                1280
Ile Leu Ala Asn Leu Asp Ala Thr Gln Trp Lys Thr Gln Arg Lys Gly
                1285                1290                1295
Ile Asn Ile Pro Ala Asp Gln Pro Ile Thr Lys Leu Lys Asn Leu Glu
                1300                1305                1310
Asp Val Val Val Pro Thr Met Glu Ile Lys Val Asp His Thr Gly Glu
    1315                1320                1325
Tyr Gly Asn Leu Val Thr Ile Gln Ser Phe Lys Ala Glu Phe Arg Leu
    1330                1335                1340
Ala Gly Gly Val Asn Leu Pro Lys Ile Ile Asp Cys Val Gly Ser Asp
1345                1350                1355                1360
Gly Lys Glu Arg Arg Gln Leu Val Lys Gly Arg Asp Asp Leu Arg Gln
                1365                1370                1375
Asp Ala Val Met Gln Gln Val Phe Gln Met Cys Asn Thr Leu Leu Gln
                1380                1385                1390
Arg Asn Thr Glu Thr Arg Lys Arg Lys Leu Thr Ile Cys Thr Tyr Lys
    1395                1400                1405
Val Val Pro Leu Ser Gln Arg Ser Gly Val Leu Glu Trp Cys Thr Gly
    1410                1415                1420
Thr Val Pro Ile Gly Glu Phe Leu Val Asn Asn Glu Asp Gly Ala His
1425                1430                1435                1440
Lys Arg Tyr Arg Pro Asn Asp Phe Ser Ala Phe Gln Cys Gln Lys Lys
                1445                1450                1455
Met Met Glu Val Gln Lys Lys Ser Phe Glu Glu Lys Tyr Glu Val Phe
                1460                1465                1470
Met Asp Val Cys Gln Asn Phe Gln Pro Val Phe Arg Tyr Phe Cys Met
                1475                1480                1485
Glu Lys Phe Leu Asp Pro Ala Ile Trp Phe Glu Lys Arg Leu Ala Tyr
```

|   |   |   |   |   |   |   |   |   |   |   |   |   |   |
|---|---|---|---|---|---|---|---|---|---|---|---|---|---|
| Thr | Arg | Ser | Val | Ala | Thr | Ser | Ser | Ile | Val | Gly | Tyr | Ile | Leu | Gly | Leu |
| 1505 | | | | 1510 | | | | 1515 | | | | | | | 1520 |
| Gly | Asp | Arg | His | Val | Gln | Asn | Ile | Leu | Ile | Asn | Glu | Gln | Ser | Ala | Glu |
| | | | | 1525 | | | | | 1530 | | | | | 1535 | |
| Leu | Val | His | Ile | Asp | Leu | Gly | Val | Ala | Phe | Glu | Gln | Gly | Lys | Ile | Leu |
| | | | 1540 | | | | | 1545 | | | | | 1550 | | |
| Pro | Thr | Pro | Glu | Thr | Val | Pro | Phe | Arg | Leu | Thr | Arg | Asp | Ile | Val | Asp |
| 1555 | | | | | | 1560 | | | | | | 1565 | | | |
| Gly | Met | Gly | Ile | Thr | Gly | Val | Glu | Gly | Val | Phe | Arg | Arg | Cys | Cys | Glu |
| 1570 | | | | | 1575 | | | | | | 1580 | | | | |
| Lys | Thr | Met | Glu | Val | Met | Arg | Asn | Ser | Gln | Glu | Thr | Leu | Leu | Thr | Ile |
| 1585 | | | | 1590 | | | | | 1595 | | | | | | 1600 |
| Val | Glu | Val | Leu | Leu | Tyr | Asp | Pro | Leu | Phe | Asp | Trp | Thr | Met | Asn | Pro |
| | | | | 1605 | | | | | 1610 | | | | | 1615 | |
| Leu | Lys | Ala | Leu | Tyr | Leu | Gln | Gln | Arg | Pro | Glu | Asp | Glu | Thr | Glu | Leu |
| | | | 1620 | | | | | 1625 | | | | | 1630 | | |
| His | Pro | Thr | Leu | Asn | Ala | Asp | Asp | Gln | Glu | Cys | Lys | Arg | Asn | Leu | Ser |
| | | 1635 | | | | | 1640 | | | | | 1645 | | | |
| Asp | Ile | Asp | Gln | Ser | Phe | Asp | Lys | Val | Ala | Glu | Arg | Val | Leu | Met | Arg |
| 1650 | | | | | | 1655 | | | | | 1660 | | | | |
| Leu | Gln | Glu | Lys | Leu | Lys | Gly | Val | Glu | Glu | Gly | Thr | Val | Leu | Ser | Val |
| 1665 | | | | | 1670 | | | | | 1675 | | | | | 1680 |
| Gly | Gly | Gln | Val | Asn | Leu | Leu | Ile | Gln | Gln | Ala | Ile | Asp | Pro | Lys | Asn |
| | | | | 1685 | | | | | 1690 | | | | | 1695 | |
| Leu | Ser | Arg | Leu | Phe | Pro | Gly | Trp | Lys | Ala | Trp | Val | | | | |
| | | | 1700 | | | | | 1705 | | | | | | | |

(2) INFORMATION FOR SEQ ID NO:3:

(i) SEQUENCE CHARACTERISTICS:
  (A) LENGTH: 6525 base pairs
  (B) TYPE: nucleic acid
  (C) STRANDEDNESS: single
  (D) TOPOLOGY: linear (xi) SEQUENCE DESCRIPTION: SEQ ID NO:3:

| | | | | | |
|---|---|---|---|---|---|
| ATATTGAGGA | TTTCTATAGA | TCTTGTTATA | AGGTTTTGAT | TCCACATCTG | GTGATTAGAA | 60 |
| GTCATTTTGA | TGAGGTGAAG | TCCATTGCTA | ATCAGATTCA | AGAGGACTGG | AAAAGTCTTC | 120 |
| TAACAGACTG | CTTTCCAAAG | ATTCTTGTAA | ATATTCTTCC | TTATTTTGCC | TATGAGGGTA | 180 |
| CCAGAGACAG | TGGGATGGCA | CAGCAAAGAG | AGACTGCTAC | CAAGGTCTAT | GATATGCTTA | 240 |
| AAAGTGAAAA | CTTATTGGGA | AAACAGTCTA | CAGGTTGGCT | GCATAGAAGA | AAAAGGTAGA | 300 |
| GTTATTTATA | ATCTTGTAAA | TCTTGGACTT | TGAGTCATCT | ATTTCTTTT | ACAGTCATCG | 360 |
| AATACTTTTG | GAAATAAGAT | TGATCACTTA | TTCATTAGTA | ATTTACCAGA | GATTGTGGTG | 420 |
| GAGTTATTGA | TGACGTTACA | TGAGCCAGCA | AATTCTAGTG | CCAGTCAGAG | CACTGACCTC | 480 |
| TGTGACTTTT | CAGGGGATTT | GGATCCTGCT | CCTAATCCAC | TCATTTTCC | ATCGCATGTG | 540 |
| ATTAAAGCAA | CATTTGCCTA | TATCAGCAAT | TGTCATAAAA | CCAAGTTAAA | AAGCATTTTA | 600 |
| GAAATTCTTT | CCAAAAGCCC | TGATTCCTAT | CAGAAAATTC | TTCTTGCCAT | ATGTGAGCAA | 660 |
| GCAGCTGAAA | CAAATAATGT | TTATAAGAAG | CACAGAATTC | TTAAAATATA | TCACCTGTTT | 720 |
| GTTAGTTTAT | TACTGAAAGA | TATAAAAAGT | GGCTTAGGAG | GAGCTTGGGC | CTTTGTTCTT | 780 |
| CGAGACGTTA | TTTATACTTT | GATTCACTAT | ATCAACCAAA | GGCCTTCTTG | TATCATGGAT | 840 |

```
GTGTCATTAC GTAGCTTCTC CCTTTGTTGT GACTTATTAA GTCAGGTTTG CCAGACAGCC      900
GTGACTTACT GTAAGGATGC TCTAGAAAAC CATCTTCATG TTATTGTTGG TACACTTATA      960
CCCCTTGTGT ATGAGCAGGT GGAGGTTCAG AAACAGGTAT TGGACTTGTT GAAATACTTA     1020
GTGATAGATA ACAAGGATAA TGAAAACCTC TATATCACGA TTAAGCTTTT AGATCCTTTT     1080
CCTGACCATG TTGTTTTTAA GGATTTGCGT ATTACTCAGC AAAAAATCAA ATACAGTAGA     1140
GGACCCTTTT CACTCTTGGA GGAAATTAAC CATTTCTCT CAGTAAGTGT TTATGATGCA      1200
CTTCCATTGA CAAGACTTGA AGGACTAAAG GATCTTCGAA GACAACTGGA ACTACATAAA     1260
GATCAGATGG TGGACATTAT GAGAGCTTCT CAGGATAATC CGCAAGATGG GATTATGGTG     1320
AAACTAGTTG TCAATTTGTT GCAGTTATCC AAGATGGCAA TAAACCACAC TGGTGAAAAA     1380
GAAGTTCTAG AGGCTGTTGG AAGCTGCTTG GGAGAAGTGG GTCCTATAGA TTTCTCTACC     1440
ATAGCTATAC AACATAGTAA AGATGCATCT TATACCAAGG CCCTTAAGTT ATTTGAAGAT     1500
AAAGAACTTC AGTGGACCTT CATAATGCTG ACCTACCTGA ATAACACACT GGTAGAAGAT     1560
TGTGTCAAAG TTCGATCAGC AGCTGTTACC TGTTTGAAAA ACATTTAGC CACAAAGACT      1620
GGACATAGTT TCTGGGAGAT TTATAAGATG ACAACAGATC CAATGCTGGC CTATCTACAG     1680
CCTTTTAGAA CATCAAGAAA AAAGTTTTTA GAAGTACCCA GATTGACAA AGAAAACCCT      1740
TTTGAAGGCC TGGATGATAT AAATCTGTGG ATTCCTCTAA GTGAAAATCA TGACATTTGG     1800
ATAAAGACAC TGACTTGTGC TTTTTTGGAC AGTGGAGGCA CAAAATGTGA AATTCTTCAA     1860
TTATTAAAGC CAATGTGTGA AGTGAAAACT GACTTTGTC AGACTGTACT TCCATACTTG      1920
ATTCATGATA TTTTACTCCA AGATACAAAT GAATCATGGA GAAATCTGCT TTCTACACAT     1980
GTTCAGGGAT TTTTCACCAG CTGTCTTCGA CACTTCTCGC AAACGAGCCG ATCCACAACC     2040
CCTGCAAACT TGGATTCAGA GTCAGAGCAC TTTTTCCGAT GCTGTTTGGA TAAAAAATCA     2100
CAAAGAACAA TGCTTGCTGT TGTGGACTAC ATGAGAAGAC AAAAGAGACC TTCTTCAGGA     2160
ACAATTTTTA ATGATGCTTT CTGGCTGGAT TTAAATTATC TAGAAGTTGC CAAGGTAGCT     2220
CAGTCTTGTG CTGCTCACTT TACAGCTTTA CTCTATGCAG AAATCTATGC AGATAAGAAA     2280
AGTATGGATG ATCAAGAGAA AAGAAGTCTT GCATTGAAG AAGGAAGCCA GAGTACAACT      2340
ATTTCTAGCT TGAGTGAAAA AAGTAAAGAA GAAACTGGAA TAAGTTTACA GGATCTTCTC     2400
TTAGAAATCT ACAGAAGTAT AGGGGAGCCA GATAGTTTGT ATGGCTGTGG TGGAGGGAAG     2460
ATGTTACAAC CCATTACTAG ACTACGAACA TATGAACACG AAGCAATGTG GGGCAAAGCC     2520
CTAGTAACAT ATGACCTCGA AACAGCAATC CCCTCATCAA CACGCCAGGC AGGAATCATT     2580
CAGGCCTTGC AGAATTTGGG ACTCTGCCAT ATTCTTTCCG TCTATTTAAA AGGATTGGAT     2640
TATGAAAATA AAGACTGGTG TCCTGAACTA GAAGAACTTC ATTACCAAGC AGCATGGAGG     2700
AATATGCAGT GGGACCATTG CACTTCCGTC AGCAAGAAG TAGAAGGAAC CAGTTACCAT      2760
GAATCATTGT ACAATGCTCT ACAATCTCTA AGAGACAGAG AATTCTCTAC ATTTTATGAA     2820
AGTCTCAAAT ATGCCAGAGT AAAAGAAGTG GAAGAGATGT GTAAGCGCAG CCTTGAGTCT     2880
GTGTATTCGC TCTATCCCAC ACTTAGCAGG TTGCAGGCCA TTGGAGAGCT GGAAAGCATT     2940
GGGGAGCTTT TCTCAAGATC AGTCACACAT AGACAACTCT CTGAAGTATA TATTAAGTGG     3000
CAGAAACACT CCCAGCTTCT CAAGGACAGT GATTTTAGTT TTCAGGAGCC TATCATGGCT     3060
CTACGCACAG TCATTTTGGA GATCCTGATG GAAAAGGAAA TGGACAACTC ACAAAGAGAA     3120
TGTATTAAGG ACATTCTCAC CAAACACCTT GTAGAACTCT CTATACTGGC CAGAACTTTC     3180
AAGAACACTC AGCTCCCTGA AAGGGCAATA TTTCAAATTA AACAGTACAA TTCAGTTAGC     3240
```

```
TGTGGAGTCT CTGAGTGGCA GCTGGAAGAA GCACAAGTAT TCTGGGCAAA AAAGGAGCAG      3300
AGTCTTGCCC TGAGTATTCT CAAGCAAATG ATCAAGAAGT GGATGCCAG  CTGTGCAGCG      3360
AACAATCCCA GCCTAAAACT TACATACACA GAATGTCTGA GGGTTTGTGG CAACTGGTTA      3420
GCAGAAACGT GCTTAGAAAA TCCTGCGGTC ATCATGCAGA CCTATCTAGA AAAGGCAGTA      3480
GAAGTTGCTG GAAATTATGA TGGAGAAAGT AGTGATGAGC TAAGAAATGG AAAAATGAAG      3540
GCATTTCTCT CATTAGCCCG GTTTTCAGAT ACTCAATACC AAAGAATTGA AACTACATG       3600
AAATCATCGG AATTTGAAAA CAAGCAAGCT CTCCTGAAAA GAGCCAAAGA GGAAGTAGGT      3660
CTCCTTAGGG AACATAAAAT TCAGACAAAC AGATACACAG TAAAGGTTCA GCGAGAGCTG      3720
GAGTGGATG  AATTAGCCCT GCGTGCACTG AAAGAGGATC GTAAACGCTT CTTATGTAAA      3780
GCAGTTGAAA ATTATATCAA CTGCTTATTA AGTGGAGAAG AACATGATAT GTGGGTATTC      3840
CGACTTTGTT CCCTCTGGCT TGAAAATTCT GGAGTTTCTG AAGTCAATGG CATGATGAAG      3900
AGAGACGGAA TGAAGATTCC AACATATAAA TTTTTGCCTC TTATGTACCA ATTGGCTGCT      3960
AGAATGGGGA CCAAGATGAT GGGAGGCCTA GGATTTCATG AAGTCCTCAA TAATCTAATC      4020
TCTAGAATTT CAATGGATCA CCCCCATCAC ACTTTGTTTA TTATACTGGC CTTAGCAAAT      4080
GCAAACAGAG ATGAATTTCT GACTAAACCA GAGGTAGCCA GAAGAAGCAG AATAACTAAA      4140
AATGTGCCTA ACAAAGCTC  TCAGCTTGAT GAGGATCGAA CAGAGGCTGC AAATAGAATA      4200
ATATGTACTA TCAGAAGTAG GAGACCTCAG ATGGTCAGAA GTGTTGAGGC ACTTTGTGAT      4260
GCTTATATTA TATTAGCAAA CTTAGATGCC ACTCAGTGGA AGACTCAGAG AAAAGGCATA      4320
AATATTCCAG CAGACCAGCC AATTACTAAA CTTAAGAATT TAGAAGATGT TGTTGTCCCT      4380
ACTATGGAAA TTAAGGTGGA CCACACAGGA GAATATGGAA ATCTGGTGAC TATACAGTCA      4440
TTTAAAGCAG AATTTCGCTT AGCAGGAGGT GTAAATTTAC CAAAAATAAT AGATTGTGTA      4500
GGTTCCGATG GCAAGGAGAG GAGACAGCTT GTTAAGGGCC GTGATGACCT GAGACAAGAT      4560
GCTGTCATGC AACAGGTCTT CCAGATGTGT AATACATTAC TGCAGAGAAA CACGGAAACT      4620
AGGAAGAGGA AATTAACTAT CTGTACTTAT AAGGTGGTTC CCCTCTCTCA GCGAAGTGGT      4680
GTTCTTGAAT GGTGCACAGG AACTGTCCCC ATTGGTGAAT TTCTTGTTAA CAATGAAGAT      4740
GGTGCTCATA AAGATACAG  GCCAAATGAT TTCAGTGCCT TCAGTGCCA  AAAGAAAATG      4800
ATGGAGGTGC AAAAAAAGTC TTTTGAAGAG AAATATGAAG TCTTCATGGA TGTTTGCCAA      4860
AATTTTCAAC CAGTTTTCCG TTACTTCTGC ATGGAAAAAT TCTTGGATCC AGCTATTTGG      4920
TTTGAGAAGC GATTGGCTTA TACGCGCAGT GTAGCTACTT CTTCTATTGT TGGTTACATA      4980
CTTGGACTTG GTGATAGACA TGTACAGAAT ATCTTGATAA ATGAGCAGTC AGCAGAACTT      5040
GTACATATAG ATCTAGGTGT TGCTTTTGAA CAGGGCAAAA TCCTTCCTAC TCCTGAGACA      5100
GTTCCTTTTA GACTCACCAG AGATATTGTG GATGGCATGG GCATTACGGG TGTTGAAGGT      5160
GTCTTCAGAA GATGCTGTGA GAAACCATG  GAAGTGATGA GAAACTCTCA GGAAACTCTG      5220
TTAACCATTG TAGAGGTAAA GTATTTTATA AGGAAGACTT TATTTTTTTT CTTACCAGGT      5280
AGACTGTGTA TCTCATCAGG AAGTCACTGA TGTGAAGAGC ACTGCTTCAT TTAACATAG       5340
GGGGATGTGG CTGGGCAGCA GAAAGGAGGA GATTGTGCAC TTAGCCTTTT CACACATCCA      5400
AAAATACTGG TTTAGAAATG CCTTCAGCCC CCTTGAGTTT CTTGGAATGT TAGAGCATTG      5460
TAAGTAGTCT CTAGTTTTCA ATTCATAAAT CAATTCTTTG ACATTTAGAT ATTCCATATG      5520
GTATTATTAT TTTTAGAATG GTTTCCATTA GGGTTACGA  AAAATCAGAA ATTTATATCT      5580
CCTCTTTCCC TGCTCAGGTT CAGAACTAAT TAGTCAGACA AAATGGAGAT CAAAATTGGT      5640
```

-continued

```
CAGCATCATT  ACTAGAGGGA  CATGGCTTAG  GAATTGAGGG  CCAAGACTAG  TTTACCTGCT    5700

GGTGCTACCC  TCAAGTACCC  TCCCTGCTGT  CTTAACTTTG  GGACAAGCTC  ACCCTGAATA    5760

GGGGTTGGGC  CTGCAGAGCA  AACACATGTA  ATCAGGATCA  CTGCCTTGTC  TTGATCCAGG    5820

GCAGAAAAAA  GGAAGTCAAA  CAAATTTCAG  TGTCTGTGCT  GTTAGTACCT  ATGCCAGTCA    5880

TTCACCAATC  TGGTAAGGGT  ATGTGAGACA  AGAAATCAGG  AGTGTGGCCT  CCCCAGGGAA    5940

GCATGGCAGG  TAGAGTGCAG  TATGGGCTTG  CCACTTTCC   ACTACTCAGC  TTTTCTTCCT    6000

TTAACCTGAT  TTATGTTGGA  CTGGCTGCAT  GTTAGTATTA  CTTTACTGC   ATTTAAAAAA    6060

CATTGATGCT  GATCAAATTC  AAACCAGGTT  TCTAGAGATG  GGGCAGGAAT  ATGTGCATTT    6120

TTAAAAATCT  CTCCTACTGT  TCCACTAGGA  TATGAGAACT  GTCTTAATTC  ATTGGCATTA    6180

ACCATTAAGC  CTGTGGTCAA  TAAGGGTGGG  CCTTTATCCC  TTGGAAGATG  AGTAACAGTC    6240

CATCAGGGTG  GTCCTGTGTG  CACCTTTATG  AACCGAGGCA  TCTTTATAGA  TCTCCTTTGG    6300

ACTGCAGGTG  GTAATACAGA  TTTTGCTACA  AGGAGTTTGC  TGAAATAGGT  CCCAATAATA    6360

CGTTGGTAAA  ATTAAATCCA  AGNCTGTGCT  ATTCCCAAGG  TTAAAAATAC  ATTCTTTTTT    6420

CTTTTACCGA  TTTCAAATTC  TGTTCATACA  TGTTGTCATT  TGTTACAGTT  TGCCATTGGT    6480

TCTGCAGTAA  GAATAAATGA  TAAGAAAATA  AAAAAAAAAA  AAAA                      6525
```

( 2 ) INFORMATION FOR SEQ ID NO:4:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear ( x i ) SEQUENCE DESCRIPTION: SEQ ID NO:4:

```
His  Glu  Pro  Ala  Asn  Ser  Ser  Ala  Ser  Gln  Ser  Thr  Asp  Leu  Cys
 1                  5                          10                      15
```

( 2 ) INFORMATION FOR SEQ ID NO:5:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear ( x i ) SEQUENCE DESCRIPTION: SEQ ID NO:5:

```
Cys  Lys  Arg  Asn  Leu  Ser  Asp  Ile  Asp  Gln  Ser  Phe  Asp  Lys  Val
 1                  5                          10                      15
```

( 2 ) INFORMATION FOR SEQ ID NO:6:

( i ) SEQUENCE CHARACTERISTICS:
        ( A ) LENGTH: 18 amino acids
        ( B ) TYPE: amino acid
        ( C ) STRANDEDNESS: single
        ( D ) TOPOLOGY: linear ( x i ) SEQUENCE DESCRIPTION: SEQ ID NO:6:

```
Pro  Glu  Asp  Glu  Thr  Glu  Leu  His  Pro  Thr  Leu  Asn  Ala  Asp  Asp  Gln
 1                  5                          10                      15

Glu  Cys
```

( 2 ) INFORMATION FOR SEQ ID NO:7:

( i ) SEQUENCE CHARACTERISTICS:
        ( A ) LENGTH: 26 amino acids
        ( B ) TYPE: amino acid (C) STRANDEDNESS: single
(D) TOPOLOGY: linear (xi) SEQUENCE DESCRIPTION: SEQ ID NO:7:

Cys Lys Ser Leu Ala Ser Phe Ile Lys Lys Pro Phe Asp Arg Gly Glu
1               5                   10                  15

Val Glu Ser Met Glu Asp Asp Thr Asn Gly
            20                  25